US012090297B2

(12) United States Patent
Reiner

(10) Patent No.: US 12,090,297 B2
(45) Date of Patent: Sep. 17, 2024

(54) ADAPTORS FOR REMOVAL OF DEBRIS AND FLUIDS FROM VENTILATOR CIRCUITS

(71) Applicant: Instrumentation Industries, Inc., Bethel Park, PA (US)

(72) Inventor: Steven C. Reiner, Pittsburgh, PA (US)

(73) Assignee: Instrumentation Industries, Inc., Bethel Park, PA (US)

( * ) Notice: Subject to any disclaimer, the term of this patent is extended or adjusted under 35 U.S.C. 154(b) by 884 days.

(21) Appl. No.: 17/061,132

(22) Filed: Oct. 1, 2020

(65) Prior Publication Data

US 2021/0093848 A1     Apr. 1, 2021

Related U.S. Application Data

(60) Provisional application No. 62/908,861, filed on Oct. 1, 2019.

(51) Int. Cl.
| | |
|---|---|
| *A61M 16/00* | (2006.01) |
| *A61M 16/08* | (2006.01) |
| *A61M 16/16* | (2006.01) |
| *A61M 16/20* | (2006.01) |
| *A61M 39/10* | (2006.01) |

(52) U.S. Cl.
CPC ........ *A61M 39/10* (2013.01); *A61M 16/0057* (2013.01); *A61M 16/0875* (2013.01); *A61M 16/16* (2013.01); *A61M 16/201* (2014.02); *A61M 16/0833* (2014.02); *A61M 2039/1077* (2013.01); *A61M 2202/0208* (2013.01); *A61M 2205/3368* (2013.01); *A61M 2207/00* (2013.01)

(58) Field of Classification Search
CPC .......... A61M 16/0003; A61M 16/0057; A61M 16/0066; A61M 16/08; A61M 16/0816; A61M 16/1045; A61M 16/1075–1095; A61M 39/10; A61M 16/105–107; A61M 16/0841; A61M 16/085; A61M 16/0858; A61M 16/0875; A61M 16/16–168; A61H 16/16–168
See application file for complete search history.

(56) References Cited

U.S. PATENT DOCUMENTS 4,063,913 A * 12/1977 Kippel .............. A61M 16/1055
                                                             55/DIG. 35
4,391,271 A     7/1983   Blanco
(Continued)

*Primary Examiner* — Bradley H Philips
*Assistant Examiner* — Savannah L Gabriel
(74) *Attorney, Agent, or Firm* — The Webb Law Firm

(57) ABSTRACT

A humidifier adaptor for evacuating fluid and/or debris from a ventilator system includes a housing having a base, a top, and at least one sidewall, which together define a chamber and an inlet in the base of the housing extending into the chamber. The inlet includes a first end configured to receive air from a humidifier, a second end in the chamber, and a sidewall. The second end of the inlet can be positioned to at least partially inhibit the fluid and/or debris from entering an interior portion of the inlet. The humidifier adaptor also includes a tangential outlet in the at least one sidewall of the housing through which the air flows substantially tangentially out of the chamber. The humidifier adaptor also includes a drain outlet in the base of the housing for removing fluid and/or debris from the ventilator system by evacuation through the chamber.

37 Claims, 21 Drawing Sheets

(56) References Cited

U.S. PATENT DOCUMENTS

| | | | | |
|---|---|---|---|---|
| 4,417,574 A | * | 11/1983 | Talonn | A61M 16/0808 96/219 |
| 4,867,153 A | * | 9/1989 | Lorenzen | A61M 16/0808 128/205.12 |
| 5,826,575 A | * | 10/1998 | Lall | A61M 16/0808 128/205.27 |
| 6,105,576 A | | 8/2000 | Clawson et al. | |
| 6,415,788 B1 | * | 7/2002 | Clawson | A61M 16/0825 128/205.12 |
| 6,494,203 B1 | * | 12/2002 | Palmer | A61M 16/0816 128/207.14 |
| 6,494,208 B1 | | 12/2002 | Morejon | |
| 6,606,994 B1 | | 8/2003 | Clark | |
| 7,390,342 B2 | * | 6/2008 | Pearson | B01D 17/045 55/423 |
| 7,549,419 B2 | | 6/2009 | Carlsen et al. | |
| 8,404,014 B2 | * | 3/2013 | Israel | B01D 39/1623 55/423 |
| 8,591,496 B2 | | 11/2013 | Caruso et al. | |
| 8,777,933 B2 | | 7/2014 | Landis et al. | |
| 8,814,838 B2 | | 8/2014 | Landis et al. | |
| 9,956,372 B2 | | 5/2018 | Polin et al. | |
| 10,130,784 B2 | | 11/2018 | Yatsevich et al. | |
| 2009/0139530 A1 | * | 6/2009 | Landis | A61M 16/0858 128/207.15 |
| 2012/0266888 A1 | | 10/2012 | Dwyer et al. | |
| 2013/0269686 A1 | | 10/2013 | Pezzano et al. | |
| 2014/0150794 A1 | * | 6/2014 | Kendrick | A61M 16/0808 128/205.12 |
| 2015/0335852 A1 | * | 11/2015 | Miller | F16K 3/029 251/366 |
| 2016/0022942 A1 | | 1/2016 | Millar et al. | |
| 2016/0279369 A1 | | 9/2016 | Cipollone et al. | |
| 2017/0224940 A1 | * | 8/2017 | Kenyon | F04D 29/4233 |
| 2017/0319809 A1 | * | 11/2017 | Biba | A61M 16/107 |
| 2018/0207388 A1 | | 7/2018 | Polin et al. | |
| 2018/0272084 A1 | | 9/2018 | Reiner | |
| 2020/0309137 A1 | * | 10/2020 | Kuriger | F04D 23/008 |

* cited by examiner

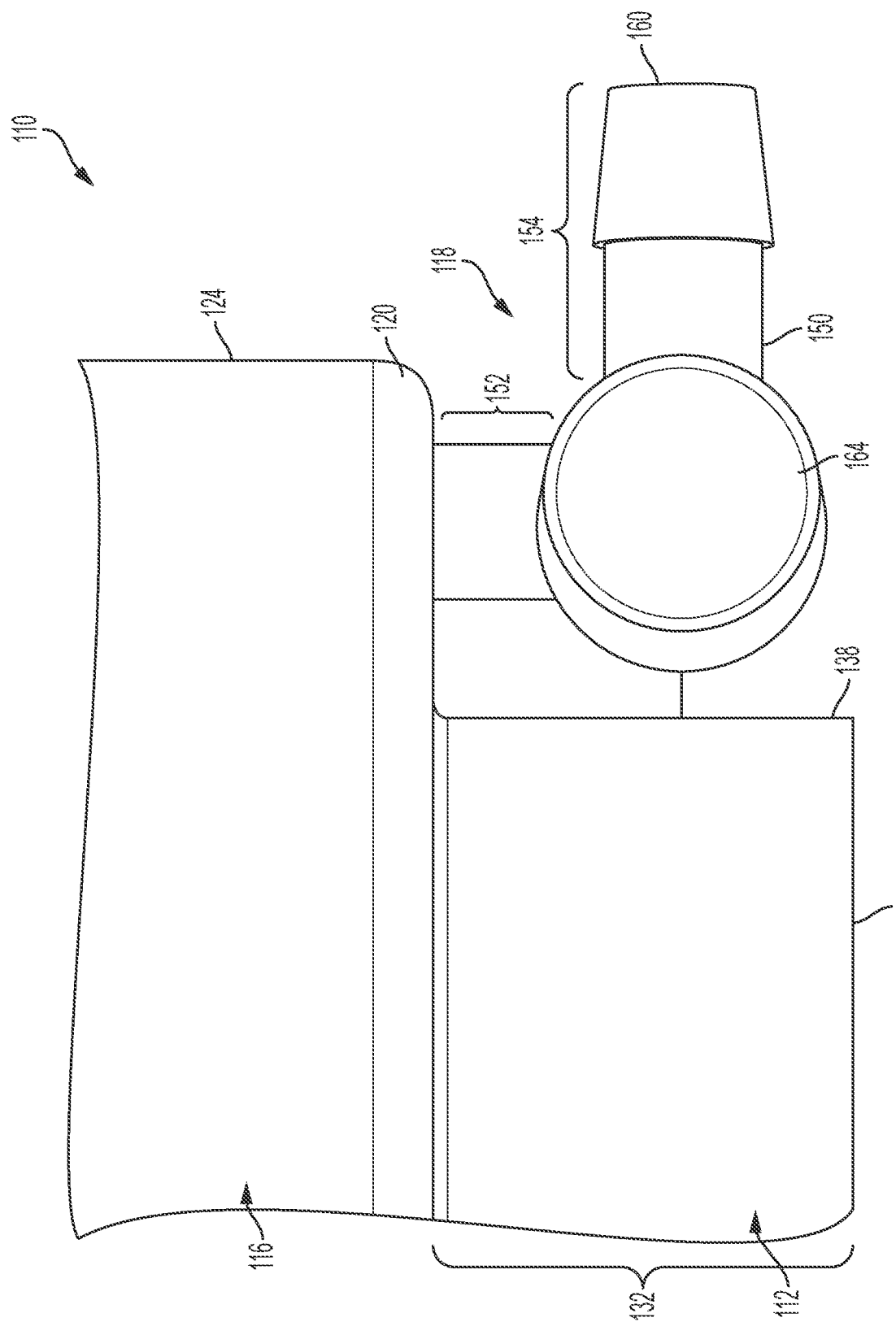

ADAPTORS FOR REMOVAL OF DEBRIS AND FLUIDS FROM VENTILATOR CIRCUITS

CROSS REFERENCE TO RELATED APPLICATION

This application claims priority to U.S. Provisional Patent Application No. 62/908,861 filed Oct. 1, 2019, entitled "Adaptors for Removal of Debris and Fluids from Ventilator Circuits," the disclosure of which is hereby incorporated by reference in its entirety.

BACKGROUND

Technical Field

The present disclosure relates to components of ventilator circuits and, in particular, to an adaptor for connecting the ventilator circuit to a suction line for removing fluids and debris, such as water, patient secretions (e.g., mucous or phlegm), and other liquids from the ventilator circuit.

Background

A ventilator or breathing circuit comprises a ventilator for providing oxygenated air to a patient and, optionally, for removing exhaled carbon dioxide from the patient. Optionally, the ventilator circuit can further comprise heater(s), humidifier(s), filter(s), suction catheter(s), and/or nebulizer(s), and may be used to deliver medicaments for inhalation, such as anesthetics. The ventilator circuit can further comprise tubing, such as an inspiratory limb or tube, connected to an inflow port or portion of a patient interface assembly, such as a nasal cannula, facemask, or endotracheal tube, for delivering the oxygenated air to a patient's airway. The circuit further comprises an expiratory limb or tube connected to an outflow port or portion of the patient interface assembly for conducting exhaled air from the patient's airway. In a closed ventilator circuit, the expiratory tube can be connected to and return exhaled air to the ventilator. Alternatively, exhaled air may be released into the atmosphere. In that case, the expiratory tube can comprise and/or be connected to filter device(s) for preventing contaminants from exhaled air from entering the ventilator or the atmosphere.

Fluids and debris, such as water and patient secretions (e.g., mucous or phlegm), from the patient's airway can collect in the tubing of the ventilator circuit. The fluids can partially occlude or clog the tubing, thereby restricting delivery of the oxygenated air to the patient. In order to remove the fluids and debris in the tubing, a user, such as a respiratory therapist, can disconnect the tubing and flush or replace segments of the tubing. Once the tubing has been cleaned or replaced, the ventilator circuit is reconnected to continue delivering oxygenated air to the patient. Disconnecting the tubing can create substantial risks for critical patients. While the ventilator circuit is disconnected, the patient is not receiving oxygenated air. For a critical patient, this interruption in oxygenated airflow can be undesirable. Also, disconnecting the ventilator circuit provides opportunities for biological contamination of the ventilator circuit. When the ventilator circuit is reconnected after flushing and/or cleaning, contaminants can be entrained in the airflow provided to the patient, which can cause infections and/or introduce bacteria into the patient's airway and respiratory system. For example, biological contamination of the ventilator circuit can cause ventilator-acquired pneumonia and related conditions.

Some ventilator circuits comprise water traps for collecting patient secretions and other fluids in the tubing. However, attaching water traps to ventilator circuits creates a number of challenges for therapists and caregivers. For example, water traps need to be positioned at a low point or the lowest point in the ventilator circuit so that secretions will flow to and collect in the trap. Accordingly, users need to be careful to avoid repositioning or elevating the water trap relative to other portions of the ventilator circuit, as may occur when a patient or medical devices near the patient are moved or repositioned. Also, traps can become clogged or may need to be cleaned, which would require the therapist to disconnect the water trap from the circuit to access an interior of the water trap. As discussed previously, disconnecting portions of the ventilator circuit can introduce biological contamination to the ventilator circuit.

Therefore, there is a need for devices and methods for clearing and/or removing secretions from ventilator circuits without requiring a therapist to disconnect the circuit or causing other inconveniences for therapists and caregivers. The devices and methods disclosed herein are intended to address such issues.

SUMMARY

According to an example of the disclosure, a humidifier adaptor for evacuating fluid and/or debris from a ventilator system comprises: a housing comprising a base, a top, and at least one sidewall extending therebetween, which together define a chamber; and an inlet in the base of the housing extending into the chamber. The inlet comprises a first end configured to receive air from a humidifier, a second end in the chamber, and a sidewall extending therebetween. The second end of the inlet can be positioned to at least partially inhibit the fluid and/or debris from entering an interior portion of the inlet. The humidifier adaptor further comprises a tangential outlet in the at least one sidewall of the housing through which the air flows substantially tangentially out of the chamber. The tangential outlet can be spaced apart from the inlet such that the fluid and/or debris is at least partially inhibited from entering the interior portion of the inlet. The humidifier adaptor further comprises a drain outlet in the base of the housing for removing fluid and/or debris from the ventilator system by evacuation through the chamber.

According to another example of the disclosure, a method for removing fluid and/or debris from a ventilator system is provided. The ventilator system comprises an inspiratory tube and a humidifier adaptor. The humidifier adaptor comprises: a housing comprising a base, a top, and at least one sidewall extending therebetween, which together define a chamber; and an inlet in the base of the housing extending into the chamber. The inlet comprises a first end configured to receive air from a humidifier, a second end in the chamber, and a sidewall extending therebetween. The second end of the inlet can be positioned to at least partially inhibit the fluid and/or debris from entering an interior portion of the inlet. The humidifier adaptor further comprises a tangential outlet in the at least one sidewall of the housing through which the air flows substantially tangentially out of the chamber to the inspiratory tube. The tangential outlet can be spaced apart from the inlet such that the fluid and/or debris is at least partially inhibited from entering the interior portion of the inlet. The humidifier adaptor further comprises a drain outlet in the base of the housing for removing the fluid and/or debris from the ventilator system by evacuation through the chamber. The method comprises steps of: tilting the inspiratory tube, thereby causing the fluid and/or debris in the inspiratory tube to pass through the inspiratory tube and outlet into the chamber defined by the housing; and actuating a suction source connected to the drain outlet to apply negative pressure to the chamber to evacuate the fluid and/or debris from the chamber through the drain outlet.

According to another example of the disclosure, a method of assembling a ventilator system comprises connecting an inlet of a humidifier adaptor to a humidifier. The humidifier adaptor can comprise: a housing comprising a base, a top, and at least one sidewall extending therebetween, which together define a chamber; and an inlet in the base of the housing extending into the chamber. The inlet can comprise a first end configured to receive air from the humidifier, a second end in the chamber, and a sidewall extending therebetween. The second end of the inlet can be positioned to at least partially inhibit the fluid and/or debris from entering an interior portion of the inlet. The humidifier adaptor further comprises a tangential outlet in the at least one sidewall of the housing through which the air flows substantially tangentially out of the chamber. The tangential outlet can be spaced apart from the inlet such that the fluid and/or debris is at least partially inhibited from entering the interior portion of the inlet. The humidifier adaptor can further comprise a drain outlet in the base of the housing for removing fluid and/or debris from the ventilator system by evacuation through the chamber. The method further comprises steps of: connecting an end of the inspiratory tube to the outlet of the humidifier adaptor; connecting an opposite end of the inspiratory tube to a patient y-connector; connecting an expiratory tube to the patient y-connector; and connecting a ventilator to the ventilator system, such that the ventilator provides oxygenated airflow to the inspiratory tube through the humidifier and the humidifier adaptor.

According to another example of the disclosure, an adaptor configured to be connected to an inspiratory tube of a ventilator system for evacuating fluid and/or debris from the ventilator system comprises a first tubular housing and a second tubular housing. The first tubular housing comprises a first inflow portion, an outflow portion, and a shoulder portion between the first inflow portion and the outflow portion. The second tubular housing is positioned circumferentially around at least a portion of the first inflow portion of the first tubular housing. The second tubular housing comprises: a second inflow portion, a drainage portion, a sidewall extending between the second inflow end portion and the drainage portion, and a drain outlet through the sidewall. The drainage portion of the second tubular housing is connected to the shoulder portion of the first tubular housing, thereby defining a fluid collection space between the first inflow portion of the first housing, the second inflow portion of the second tubular housing, and the shoulder portion of the first tubular housing. The fluid and/or debris collected in the fluid collection space drains from the adaptor through the drain outlet of the second tubular housing.

According to another example of the disclosure, a method for removing fluid and/or debris from a ventilator system is provided. The ventilator system comprises an inspiratory tube and an adaptor connected to the inspiratory tube. The adaptor comprises a first tubular housing and a second tubular housing. The first tubular housing comprises a first inflow portion, an outflow portion, and a shoulder portion between the first inflow portion and the outflow portion. The second tubular housing is positioned circumferentially around at least a portion of the first inflow portion of the first tubular housing. The second tubular housing comprises: a second inflow portion connected to the inspiratory tube, a drainage portion, a sidewall extending between the second inflow end portion and the drainage portion, and a drain outlet through the sidewall. The drainage portion of the second tubular housing is connected to the shoulder portion of the first tubular housing, thereby defining a fluid collection space between the first inflow portion of the first housing, the second inflow portion of the second tubular housing, and the shoulder portion of the first tubular housing. The fluid and/or debris collected in the fluid collection space drains from the adaptor through the drain outlet of the second tubular housing. The method comprises steps of: tilting the inspiratory tube, thereby causing the fluid and/or debris in the inspiratory tube to pass through the inspiratory tube and into the fluid collection space of the adaptor; and actuating a suction source connected to the drain outlet of the adaptor, thereby causing the fluid and/or debris in the fluid collection space to be evacuated from the adaptor through the drain outlet.

Non-limiting examples of the present invention will now be described in the following numbered clauses:

Clause 1: A humidifier adaptor for evacuating fluid and/or debris from a ventilator system, comprising: (a) a housing comprising a base, a top, and at least one sidewall extending therebetween, which together define a chamber; (b) an inlet in the base of the housing extending into the chamber, the inlet comprising a first end configured to receive air from a humidifier, a second end in the chamber, and a sidewall extending therebetween, the second end of the inlet being positioned to at least partially inhibit the fluid and/or debris from entering an interior portion of the inlet; (c) a tangential outlet in the at least one sidewall of the housing through which the air flows substantially tangentially out of the chamber, wherein the tangential outlet is spaced apart from the inlet such that the fluid and/or debris is at least partially inhibited from entering the interior portion of the inlet; and (d) a drain outlet in the base of the housing for removing the fluid and/or debris from the ventilator system by evacuation through the chamber.

Clause 2: The humidifier adaptor of clause 1, wherein the housing comprises a cylindrical housing.

Clause 3: The humidifier adaptor of clause 1 or clause 2, wherein the inlet extends into the chamber such that at least a portion of the fluid and/or debris collects in the chamber without entering into the interior portion of the inlet.

Clause 4: The humidifier adaptor of any of clauses 1-3, wherein the second end of the inlet is spaced apart from the base of the housing by a vertical distance of about 2.5 cm to about 10 cm.

Clause 5: The humidifier adaptor of any of clauses 1-4, wherein the first end of the inlet is external to the housing.

Clause 6: The humidifier adaptor of any of clauses 1-5, wherein the sidewall of the inlet is integral with the base of the housing.

Clause 7: The humidifier adaptor of any of clauses 1-6, wherein the inlet is configured to be mounted to an outflow port of the humidifier.

Clause 8: The humidifier adaptor of any of clauses 1-7, wherein the tangential outlet is in an upper portion of the sidewall of the housing.

Clause 9: The humidifier adaptor of any of clauses 1-8, wherein at least a portion of the tangential outlet is below the second end of the inlet.

Clause 10: The humidifier adaptor of any of clauses 1-9, wherein the tangential outlet comprises an external end outside of the housing configured to connect to an inhalation tube of the ventilator system and a sidewall extending from the external end to the housing.

Clause 11: The humidifier adaptor of clause 10, wherein the sidewall of the tangential outlet is integral with the sidewall of the housing.

Clause 12: The humidifier adaptor of any of clauses 1-11, wherein a central axis of the inlet is generally perpendicular to a central axis of the tangential outlet.

Clause 13: The humidifier adaptor of any of clauses 1-11, wherein a central axis of the tangential outlet is tangent to any co-planar arc centered on a central axis of the inlet.

Clause 14: The humidifier adaptor of any of clauses 1-11, wherein an angle θ between a central axis of the tangential outlet and a line tangent to an arc defined by an inner surface of the sidewall of the housing at a point of intersection between the central axis of the tangential outlet and the arc is from 20° to 70°.

Clause 15: The humidifier adaptor of any of clauses 1-11, wherein a central axis of the inlet is spaced apart from a central axis of the tangential outlet by a distance of about 10 mm to about 50 mm.

Clause 16: The humidifier adaptor of any of clauses 1-15, wherein the drain outlet is configured to receive negative pressure from a suction source.

Clause 17: The humidifier adaptor of clause 16, wherein the drain outlet comprises a drain tube comprising a first end in the base of the housing and a second end, opposite the first end, configured to be connected to the suction source.

Clause 18: The humidifier adaptor of clause 17, wherein the drain tube is integral with the base of the housing.

Clause 19: The humidifier adaptor of any of clauses 1-18, wherein the drain outlet comprises a valve for restricting fluid flow from the chamber through the drain outlet.

Clause 20: The humidifier adaptor of any of clauses 1-19, further comprising a splash shield extending into the chamber from the top of the housing towards the second end of the inlet, the splash shield being positioned to at least partially inhibit the fluid and/or debris from entering the interior portion of the inlet.

Clause 21: The humidifier adaptor of any of clauses 1-20, wherein the sidewall of the inlet is cylindrical and the splash shield comprises an arcuate body sized to partially surround an outer surface of the sidewall of the inlet.

Clause 22: The humidifier adaptor of any of clauses 1-21, wherein the housing comprises a port configured to receive a temperature probe for measuring a temperature in the chamber.

Clause 23: The humidifier adaptor of any of clauses 1-21, further comprising a temperature probe, wherein the housing comprises a port configured to receive the temperature probe, such that a sensory portion of the probe is positioned in the chamber.

Clause 24: A method for removing fluid and/or debris from a ventilator system, wherein the ventilator system comprises an inspiratory tube and an adaptor, the adaptor comprising: (a) a housing comprising a base, a top, and at least one sidewall extending therebetween, which together define a chamber; (b) an inlet in the base of the housing extending into the chamber, the inlet comprising a first end configured to receive air from a humidifier, a second end in the chamber, and a sidewall extending therebetween, the second end of the inlet being positioned to at least partially inhibit the fluid and/or debris from entering an interior portion of the inlet; (c) a tangential outlet in the at least one sidewall of the housing through which the air flows substantially tangentially out of the chamber to the inspiratory tube, wherein the tangential outlet is spaced apart from the inlet such that the fluid and/or debris is at least partially inhibited from entering the interior portion of the inlet; (d) and a drain outlet in the base of the housing for removing the fluid and/or debris from the ventilator system by evacuation through the chamber, the method comprising: tilting the inspiratory tube, thereby causing the fluid and/or debris in the inspiratory tube to pass through the inspiratory tube and outlet into the chamber defined by the housing; and actuating a suction source connected to the drain outlet to apply negative pressure to the chamber to evacuate the fluid and/or debris from the chamber through the drain outlet.

Clause 25: The method of clause 24, wherein the inlet is mounted to an outflow port of the humidifier.

Clause 26: The method of clause 24 or clause 25, wherein the drain outlet comprises a drain tube comprising a first end in the base of the housing and a second end, opposite the first end, configured to be connected to the suction source.

Clause 27: The method of any of clauses 24-26, wherein the drain outlet further comprises a valve for restricting a flow of the fluid and/or debris from the chamber.

Clause 28: The method of any of clauses 24-27, further comprising opening the valve so that the negative pressure from the suction source is applied to the chamber through the drain outlet.

Clause 29: The method of clause 27 or clause 28, further comprising closing the valve after the fluid and/or debris is removed from the chamber.

Clause 30: The method of any of clauses 27-29, wherein the valve comprises a manually actuated valve which is opened or closed by pressing on a piston of the valve.

Clause 31: A method of assembling a ventilator system, comprising: connecting an inlet of a humidifier adaptor to a humidifier, wherein the humidifier adaptor comprises: (a) a housing comprising a base, a top, and at least one sidewall extending therebetween, which together define a chamber; (b) an inlet in the base of the housing extending into the chamber, the inlet comprising a first end configured to receive air from the humidifier, a second end in the chamber, and a sidewall extending therebetween, the second end of the inlet being positioned to at least partially inhibit fluid and/or debris from entering an interior portion of the inlet; (c) a tangential outlet in the at least one sidewall of the housing through which the air flows substantially tangentially out of the chamber, wherein the tangential outlet is spaced apart from the inlet such that the fluid and/or debris is at least partially inhibited from entering the interior portion of the inlet; (d) and a drain outlet in the base of the housing for removing the fluid and/or debris from the ventilator system by evacuation through the chamber; directly or indirectly connecting an end of an inspiratory tube to the outlet of the humidifier adaptor; connecting an opposite end of the inspiratory tube to a patient y-connector; connecting an expiratory tube to the patient y-connector; and connecting a ventilator to the ventilator system, such that the ventilator provides oxygenated airflow to the inspiratory tube through the humidifier and the humidifier adaptor.

Clause 32: The method of clause 31, further comprising connecting a patient side port of the y-connector to a patient interface assembly to conduct air to and from a patient.

Clause 33: The method of clause 31 or clause 32, wherein connecting the humidifier adaptor to the humidifier comprises inserting an outflow port of the humidifier into the inlet of the humidifier adaptor through the first end of the inlet.

Clause 34: The method of any of clauses 31-33, wherein the drain outlet comprises a drain tube comprising an open first end in the base of the housing and an open second end, opposite the first end, the method further comprising connecting the open second end of the drain tube to a suction source for applying negative pressure to the chamber.

Clause 35: An adaptor configured to be connected to an inspiratory tube of a ventilator system for evacuating fluid and/or debris from the ventilator system, the adaptor comprising: a first tubular housing comprising a first inflow portion, an outflow portion, and a shoulder portion between the first inflow portion and the outflow portion; and a second tubular housing positioned circumferentially around at least a portion of the first inflow portion of the first tubular housing, the second tubular housing comprising: a second inflow portion, a drainage portion, a sidewall extending between the second inflow portion and the drainage portion, and a drain outlet through the sidewall, wherein the drainage portion of the second tubular housing is connected to the shoulder portion of the first tubular housing, thereby defining a fluid collection space between the first inflow portion of the first tubular housing, the second inflow portion of the second tubular housing, and the shoulder portion of the first tubular housing, and wherein the fluid and/or debris collected in the fluid collection space drains from the adaptor through the drain outlet of the second tubular housing.

Clause 36: The adaptor of clause 35, wherein the first inflow portion of the first tubular housing extends axially from the outflow portion of the first tubular housing.

Clause 37: The adaptor of clause 35 or clause 36, wherein the first tubular housing and the second tubular housing are coaxially aligned along a common longitudinal axis.

Clause 38: The adaptor of any of clauses 35-37, wherein the fluid collection space is defined between an outer surface of the first inflow portion of the first tubular housing, an inner surface of the second inflow portion of the second tubular housing, and an outer surface of the shoulder portion of the first tubular housing.

Clause 39: The adaptor of any of clauses 35-38, wherein the second inflow portion of the second tubular housing has an outer diameter larger than an outer diameter of the first inflow portion, and the second inflow portion is sized to be inserted into and connect to the inspiratory tube of the ventilator system.

Clause 40: The adaptor of any of clauses 35-39, wherein the first inflow portion of the first tubular housing has a first inner diameter, and the outflow portion of the first tubular housing has a second inner diameter, the second inner diameter being larger than the first inner diameter.

Clause 41: The adaptor of clause 40, wherein the outflow portion is sized to receive and connect to a port of a patient y-connector of the ventilator system.

Clause 42: The adaptor of any of clauses 35-41, wherein the fluid collection space is configured to contain at least about 3 mL of the fluid and/or debris.

Clause 43: The adaptor of any of clauses 35-42, wherein the drain outlet comprises a drain tube comprising an open first end in the sidewall of the second tubular housing, an open second end opposite the first end, and a sidewall extending therebetween.

Clause 44: The adaptor of clause 43, wherein the drain tube defines a fluid path for draining the fluid and/or debris from the fluid collection space.

Clause 45: The adaptor of clause 43 or clause 44, wherein the drain tube further comprises a valve which, when closed, prevents the fluid and/or debris from draining from the fluid collection space.

Clause 46: The adaptor of clause 46, wherein the valve is a manually-actuated valve.

Clause 47: The adaptor of any of clauses 43-46, wherein the open second end of the drain tube is configured to be connected to a suction source for drawing the fluid and/or debris from the fluid collection space of the adaptor.

Clause 48: The adaptor of any of clauses 35-47, wherein the first tubular housing and the second tubular housing are fixedly connected together.

Clause 49: The adaptor of any of clauses 35-48, wherein the first tubular housing and the second tubular housing are separately molded and connected together by at least one of ultrasonic welding, screw threads, solvent bonding, or a tapered press fit connection.

Clause 50: A method for removing fluid and/or debris from a ventilator system, the ventilator system comprising an inspiratory tube and an adaptor connected to the inspiratory tube, the adaptor comprising: a first tubular housing comprising a first inflow portion, an outflow portion, and a shoulder portion between the first inflow portion and the outflow portion; and a second tubular housing positioned circumferentially around at least a portion of the first inflow portion of the first tubular housing, the second tubular housing comprising: a second inflow portion connected to the inspiratory tube, a drainage portion, a sidewall extending between the second inflow portion and the drainage portion, and a drain outlet through the sidewall, wherein the drainage portion of the second tubular housing is connected to the shoulder portion of the first tubular housing, thereby defining a fluid collection space between the first inflow portion of the first tubular housing, the second inflow portion of the second tubular housing, and the shoulder portion of the first tubular housing, and wherein the fluid and/or debris collected in the fluid collection space drains from the adaptor through the drain outlet of the second tubular housing, the method comprising: tilting the inspiratory tube, thereby causing the fluid and/or debris in the inspiratory tube to pass through the inspiratory tube and into the fluid collection space of the adaptor; and actuating a suction source connected to the drain outlet of the adaptor, thereby causing the fluid and/or debris in the fluid collection space to be evacuated from the adaptor through the drain outlet.

Clause 51: The method of clause 50, wherein the fluid collection space is defined between an outer surface of the first inflow portion of the first tubular housing, an inner surface of the second inflow portion of the second tubular housing, and an outer surface of the shoulder portion of the first tubular housing.

Clause 52: The method of clause 50 or clause 51, wherein the drain outlet comprises a drain tube comprising an open first end in the sidewall of the second tubular housing and an open second end, opposite the first end, configured to be connected to the suction source.

Clause 53: The method of clause 52, wherein the drain outlet further comprises a valve positioned between the first end and the second end of the drain tube for restricting a flow of the fluid and/or debris from the adaptor.

Clause 54: The method of clause 53, further comprising opening the valve so that negative pressure from the suction source is applied to the fluid collection space through the drain outlet.

Clause 55: The method of clause 53 or clause 54, further comprises closing the valve after the fluid and/or debris is evacuated from the fluid collection space of the adaptor.

Clause 56: The method of any of clauses 53-55, wherein the valve comprises a manually-actuated valve which is opened or closed by pressing on a piston of the valve.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

Further features and other examples and advantages will become apparent from the following detailed description made with reference to the drawings in which:

FIG. 3A is a front view of the integral valve of the humidifier adaptor of FIG. 2A;

DETAILED DESCRIPTION OF THE INVENTION

Figure 1:
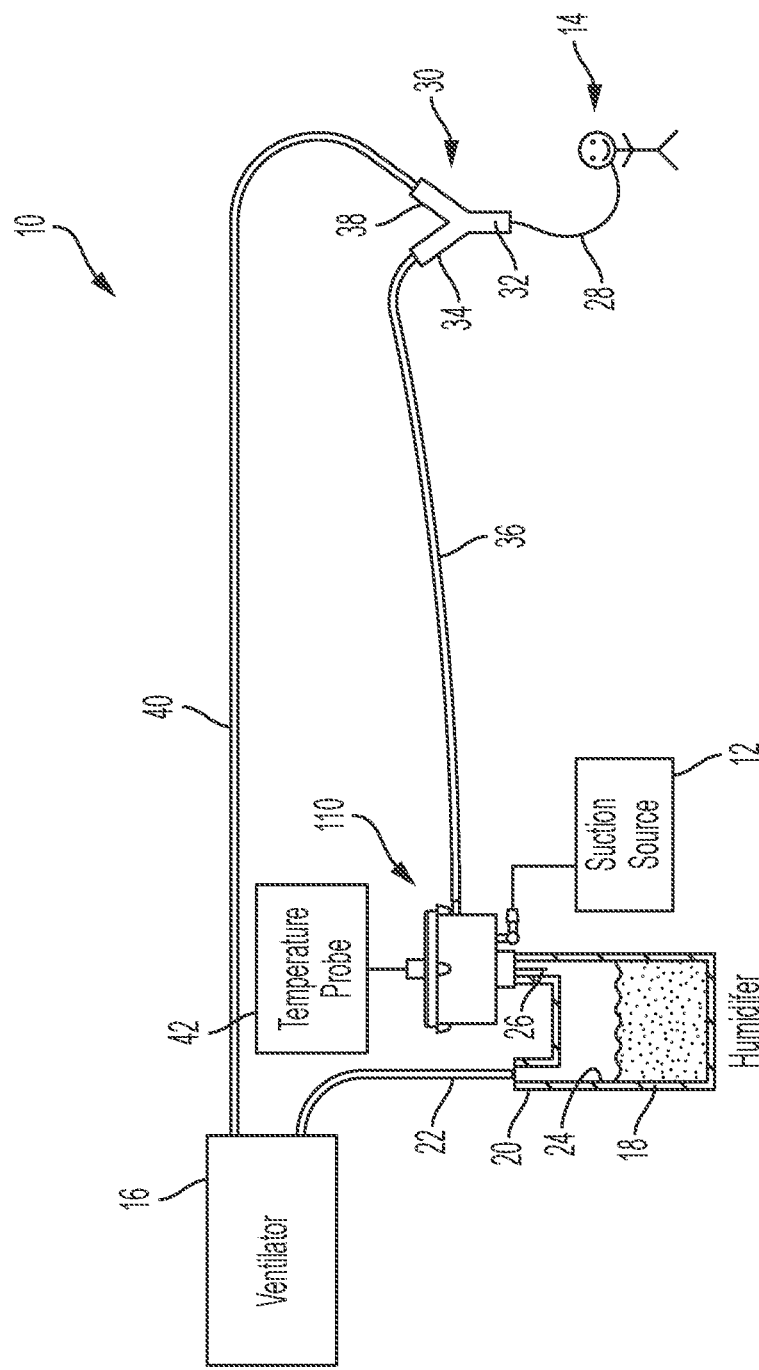
FIG. 1 is a schematic drawing of a ventilator system including a humidifier adaptor, according to an example of the disclosure.

As used herein, the singular form of "a", "an", and "the" include plural referents unless the context clearly states otherwise.

As used herein, the terms "right", "left", "top", and derivatives thereof shall relate to the invention as it is oriented in the drawing figures. The term "proximal" refers to the portion of a medical device or assembly which is closest to and/or in contact with the patient. The term "distal" refers to the opposite end of the medical device or assembly from the proximal end. Thus, the term "distal" refers to a portion of a medical device or assembly which is farthest away from the patient. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

Unless otherwise indicated, all numbers expressing quantities of ingredients, reaction conditions, dimensions, physical characteristics, and so forth used in the specification and claims are to be understood as being modified in all instances by the term "about." Unless indicated to the contrary, the numerical parameters set forth in the following specification and attached claims are approximations that can vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10. That is, all subranges beginning with a minimum value equal to or greater than 1 and ending with a maximum value equal to or less than 10, and all subranges in between, e.g., 1 to 6.3, or 5.5 to 10, or 2.7 to 6.1.

With reference to the figures, the present disclosure is generally directed to embodiments of access ports or adaptors 110, 410 attached to and/or provided in ventilator circuits or systems 10 for providing an access or drainage point for removing fluids and debris from tubing and components of the ventilator circuit or system 10 in a safe and convenient manner. As used herein, "debris" can refer to solid materials, such as biological materials and tissues, expelled from the patient's airway and/or respiratory system into the ventilator circuit or system 10. As used herein, "fluids" can refer to liquids and/or liquids including dispersed solids. For example, fluids can comprise water and/or patient secretions, such as mucus or phlegm. The adaptors 110, 410 disclosed herein can be configured to remove the fluids and debris from the ventilator circuit or system 10 without needing to disconnect elements of the ventilator circuit or system 10.

In some examples, the fluids and debris can be removed from the circuit or system 10 through the adaptor(s) 110, 410 by gravity. In other examples, the adaptors 110, 410 can be configured to be removably connected to suction sources 12, such as suction catheters, suction lines or suction ports found in medical facilities (e.g., suction ports mounted in building walls), and/or stationary or portable vacuum pumps. When the suction source 12 is activated and/or when a valve of the adaptor 110, 410 is opened, negative pressure can be applied through the suction line into an interior of the adaptor 110, 410. An amount or intensity of negative pressure applied to the interior of the adaptor 110, 410 through the suction line can be a standard amount provided by the medical facility's suction outlet. In some examples, the outlet suction pressure can be controlled by a pressure regulator. In some examples, negative pressure applied to the interior of the adaptor 110, 410 to remove fluid and/or debris can be between −10 kPa and −80 kPa, or any convenient pressure. The applied negative pressure can be used to remove the fluids and debris from the adaptor 110, 410. In some instances, a user may tilt or adjust portions of the ventilator circuit or system 10 so that fluid and/or debris flows freely into the interior of the adaptor 110, 410. For example, a user may tilt inspiratory tubing of the ventilator circuit or system 10 towards the adaptor 110 to increase debris and/or fluid flow through the tubing into components of the adaptor 110. Beneficially, the adaptors 110, 410 can be positioned at a variety of different points along the ventilator circuit or system 10 and/or tubing. The adaptors 110, 410 do not need to be positioned at a low point or at the lowest point in the ventilator circuit or system 10, as is the case for a water trap.

Ventilator System

FIG. 1 shows a non-limiting example of a ventilator circuit or system 10 according to the present invention, which is configured to provide oxygenated air to an airway of a patient 14. The ventilator circuit or system 10 comprises a mechanical ventilator 16 fluidly connected to a humidifier 18 for preparing the air being delivered to the patient 14. The ventilator 16 can be a portable or stationary mechanical ventilator, as are known in the art. Non-limiting examples of mechanical ventilators 16 that can be used with the ventilator circuits or systems 10 described herein include the Puritan Bennett™ 840 ventilator from Medtronic Inc., Drager Evita Infinity® V500 ventilator from Dragerwerk AG & Co. KGaA, and Respironics V200 ventilator from Koninklijke Philips N.V. Non-limiting examples of humidifiers 18 that can be used with the ventilator circuits or systems 10 described herein include the MR850 Heated Humidifier (which uses the MR290 Humidification Chamber) from Fisher & Paykel Healthcare Ltd., the Hudson RCI NEPTUNE® Heated Humidifier from Teleflex Inc., and the HAMILTON-H900 Humidifier from Hamilton Medical AG. The humidifier 18 generally comprises an inflow port 20 connected to the ventilator 16 through, for example, a length of tubing 22, a container 24 containing liquid to be introduced into airflow passing through the humidifier 18, and an outflow port 26 for introducing the humidified air into the ventilator circuit or system 10.

The ventilator circuit or system 10 further comprises a patient interface assembly 28 connected to a patient wye or y-connector 30. The patient wye or y-connector 30 can be a commercially available patient wye connector, as is known in the art, such as a plastic single-use or reusable wye connector. For example, the y-connector 30 can be formed from a polycarbonate or similar rigid plastic material. The patient interface assembly 28 can comprise, for example, an endotracheal tube, a nasotracheal tube, or a tracheal tube. In other examples, the patient interface assembly 28 can comprise a nasal cannula, breathing facemask, or similar structure for providing oxygenated air to the patient 14. The y-connector 30 comprises three connection points or ports, as follows. A patient-side port 32 is connected to the patient interface assembly 28. An inflow port 34 of the y-connector 30 is connected to an inspiratory line or tube 36 extending from the outflow port 26 of the humidifier 18. An outflow port 38 of the y-connector 30 is connected to an expiratory line or tube 40. The expiratory tube 40 can extend from the y-connector 30 to the ventilator 16, thereby forming a closed ventilation circuit. In other examples, the expiratory tube 40 can be connected to a filter unit or device (not shown) for releasing exhaled air to atmosphere. The expiratory tube 40 and the inspiratory tube 36 can comprise conventional medical tubing commonly used in breathing circuits and breathing tubes. For example, the medical tubing can be corrugated tubing formed from a flexible plastic material. The tubing can have an inner diameter of about 10 mm to about 25 mm, or about 22 mm. The tubing can be formed from various plastic materials including silicone, ethylene vinyl acetate, polyethylene, and similar materials.

Figure 5:
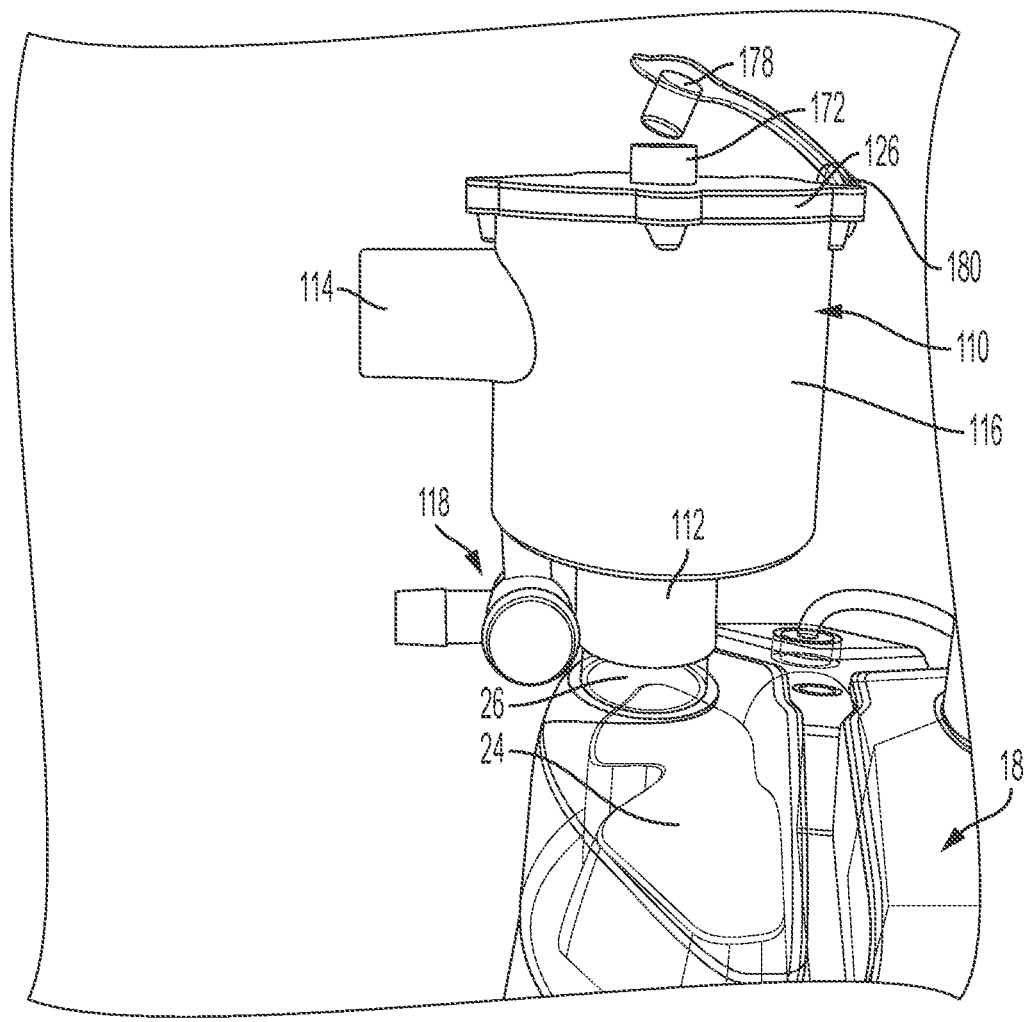
FIG. 5 is a perspective view of the humidifier adaptor of FIG. 2A mounted to a humidifier, according to an example of the disclosure.
Figure 6:
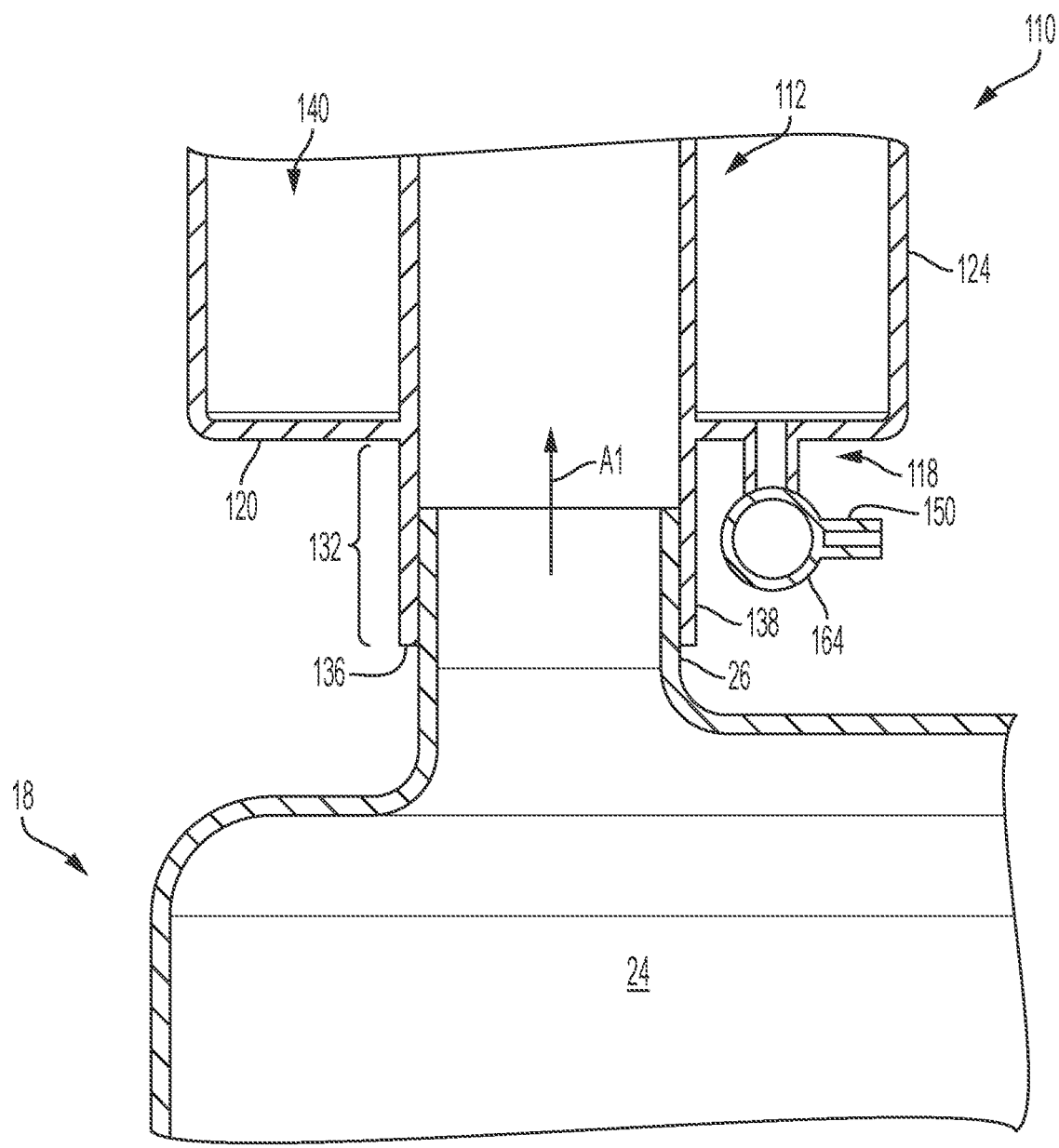
FIG. 6 is a cross-sectional view of a portion of the humidifier adaptor of FIG. 2A mounted to a humidifier, according to an example of the disclosure.

As shown in FIG. 1, the ventilator circuit or system 10 further comprises a humidifier adaptor 110 for connecting the ventilator circuit or system 10 to the suction source 12. The humidifier adaptor 110 can be configured to remove or evacuate fluid and/or debris from the ventilator circuit or system 10. The humidifier adaptor 110 can be mounted, for example, to the outflow port 26 of the humidifier 18. For example, the outflow port 26 can extend vertically from a top portion of the humidifier 18. In that case, as shown in FIGS. 5 and 6, the humidifier adaptor 110 may rest on top of the outflow port 26. In some examples, the outflow port 26 of the humidifier 18 may be inserted into a corresponding inflow port, inflow member, or inlet 112 of the humidifier adaptor 110 to establish fluid communication between the container 24 of the humidifier 18 and an interior of the humidifier adaptor 110. As described in further detail herein, the humidifier adaptor 110 further comprises an outflow port, outflow member, or outlet 114 (shown in FIGS. 2A-2E) configured to be connected to the inspiratory tube 36 of the ventilator circuit or system 10. Oxygenated airflow passes from the humidifier 18 through the humidifier adaptor 110 to the inspiratory tube 36 as shown by arrows, A1, A2, and A3 (shown in FIG. 2C). The provided oxygenated airflow is delivered from the inspiratory tube 36 to the patient through the y-connector 30 and the patient interface assembly 28.

Humidifier Adaptor

FIGS. 2A-6 show the humidifier adaptor 110 in further detail. As previously described, the humidifier adaptor 110 is configured to collect fluids and/or debris that becomes trapped in the inspiratory tube 36 or other portions of a ventilator circuit or system 10. The humidifier adaptor 110 is configured to be connected to the suction source 12 for applying negative pressure to an interior of the humidifier adaptor 110 to remove or evacuate the fluids and/or debris from the ventilator circuit or system 10. As shown in FIGS. 2A-2D, the humidifier adaptor 110 comprises a housing 116, the inlet 112, the outlet 114, and a suction port or drain outlet 118. The housing 116, inlet 112, outlet 114, and drain outlet 118 can be integral structures formed, for example, by a suitable molding process, such as injection molding. In other examples, components of the humidifier adaptor 110 can be molded and/or formed separately and connected together using adhesives, fasteners, or welding techniques, as are known in the art. As described in further detail herein, the housing 116 and components of the humidifier adaptor 110 can comprise a variety of rigid materials commonly used for forming medical devices. For example, the housing 116 and other components of the humidifier adaptor 110 can be formed from rigid plastics, such as high density polyethylene, polyethylene terephthalate, polyvinylchloride, polycarbonates, and similar materials. In other examples, components of the housing 116 can be formed from metals, such as stainless steel, or glass.

In some examples, the housing 116 comprises a base 120, a top 122, and at least one sidewall 124 extending therebetween. The base 120, top 122, and at least one sidewall 124 can enclose or define a chamber 128 (shown in FIG. 2D). For example, the housing 116 can comprise a cylindrical housing comprising a closed or partially closed base 120 and a cylindrical sidewall 124 extending therefrom. The top 122 can be closed or open. In some examples, the top 122 can be covered by a cap 126. The cap 126 can be fixedly or removably connected to the sidewall 124 of the housing 116. The chamber 128 is generally sized to contain fluids and/or debris collected from the ventilator circuit or system 10 until the fluids and/or debris can be removed, drained, or evacuated from the chamber 128. For example, the housing 116 can be configured to contain about 20 mL to about 200 mL, or about 50 mL, of fluids and/or debris. In some examples, the housing 116 can be from about 2 cm to about 20 cm in diameter, preferably about 6 cm in diameter, and about 2 cm to about 20 cm tall, preferably about 5.5 cm tall. The sidewall 124 can be about 1 m to 5 mm thick, or any desired thickness.

The humidifier adaptor 110 further comprises the inlet 112. The inlet 112 is positioned in the base 120 of the housing 116 and protrudes or extends through the base 120 into the chamber 128. The inlet 112 can be configured to provide ventilation airflow into the chamber 128, in a direction of arrow A1 and arrow A2 (shown in FIG. 2C). In some examples, the inlet 112 comprises a first portion 132 external to the housing 116 comprising an external or first end 136 configured to receive air from the humidifier 18. As described in further detail herein, the external or first end 136 of the inlet 112 can be configured to be connected to or mounted on the outflow port 26 of the humidifier 18 to establish fluid communication between the humidifier 18 and the chamber 128. The inlet 112 can further comprise a second portion 130 inside the housing 116 comprising an inner or second end 134. The inlet 112 can further comprise a sidewall 138 extending between the external or first end 136 and the inner or second end 134 thereof. The sidewall 138 of the inlet 112 can be integral with the base 120 of the housing 116. In other examples, the inlet 112 can be a separately molded or formed structure mounted into an opening in the base 120 of the housing 116 and fixed in place using adhesives or welding techniques, as are known in the art.

Figure 2A:
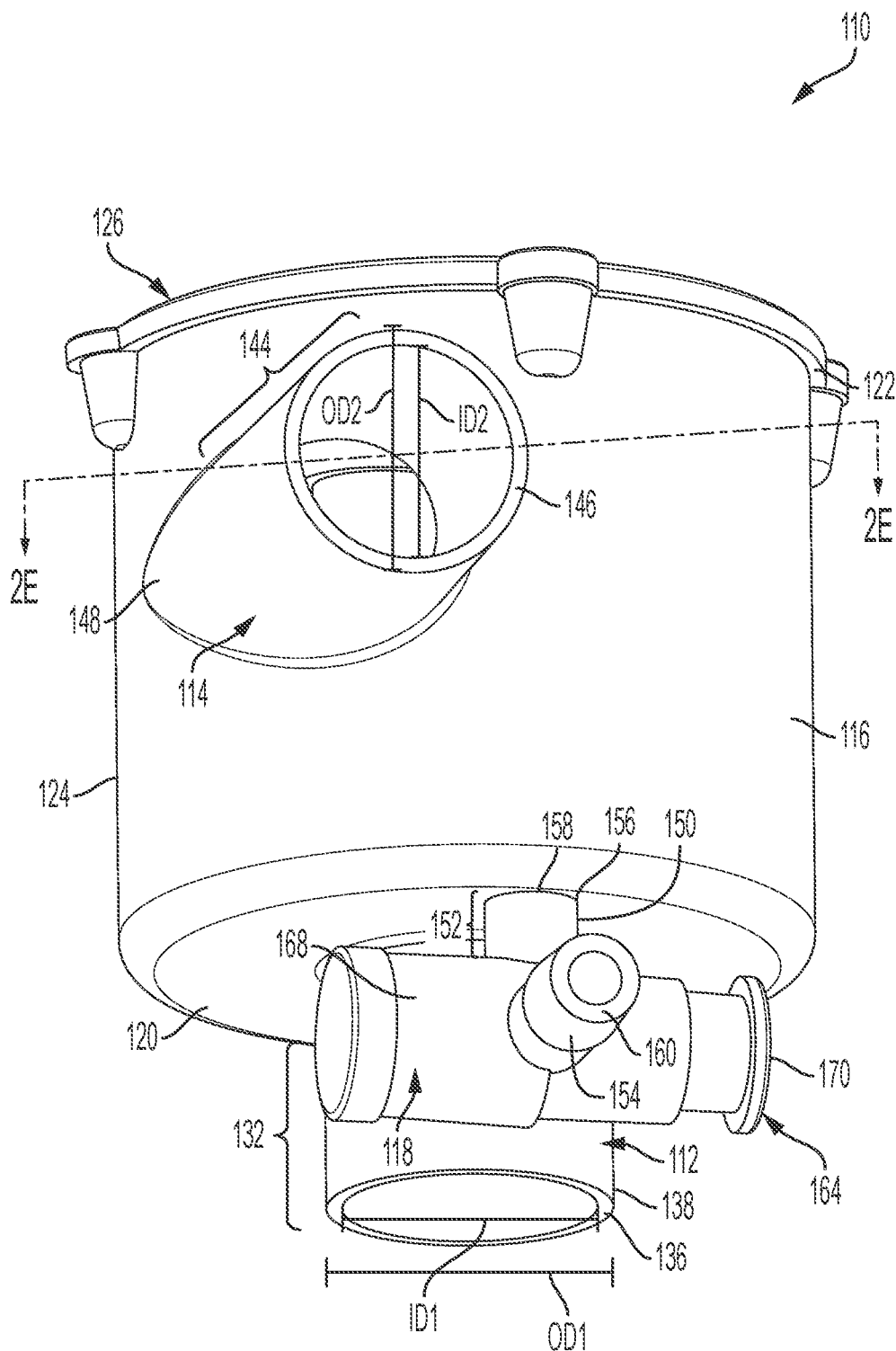
FIG. 2A is a perspective view of a humidifier adaptor for a ventilator system, according to an example of the disclosure.
Figure 2B:
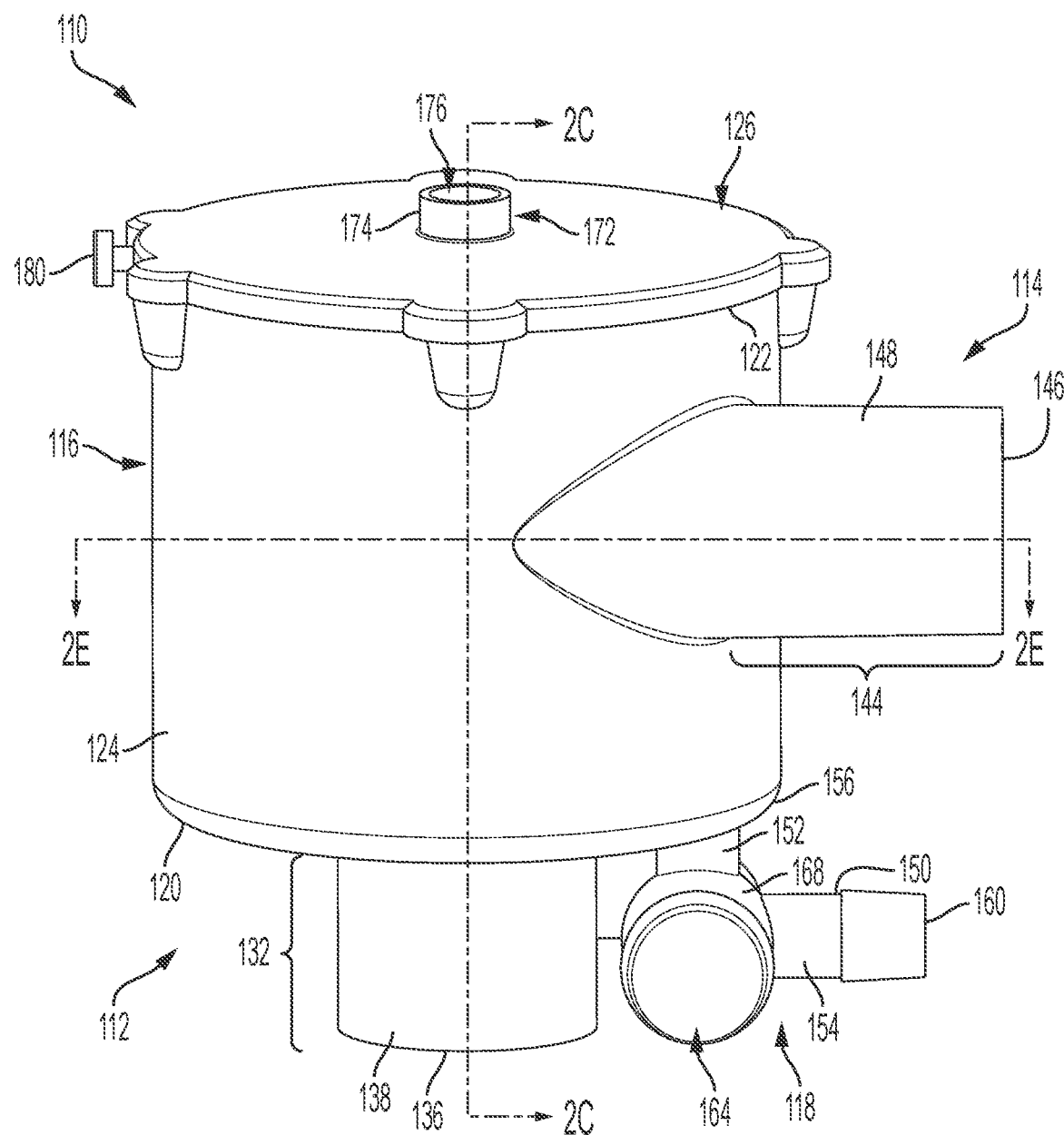
FIG. 2B is another perspective view of the humidifier adaptor of FIG. 2A.
Figure 2C:
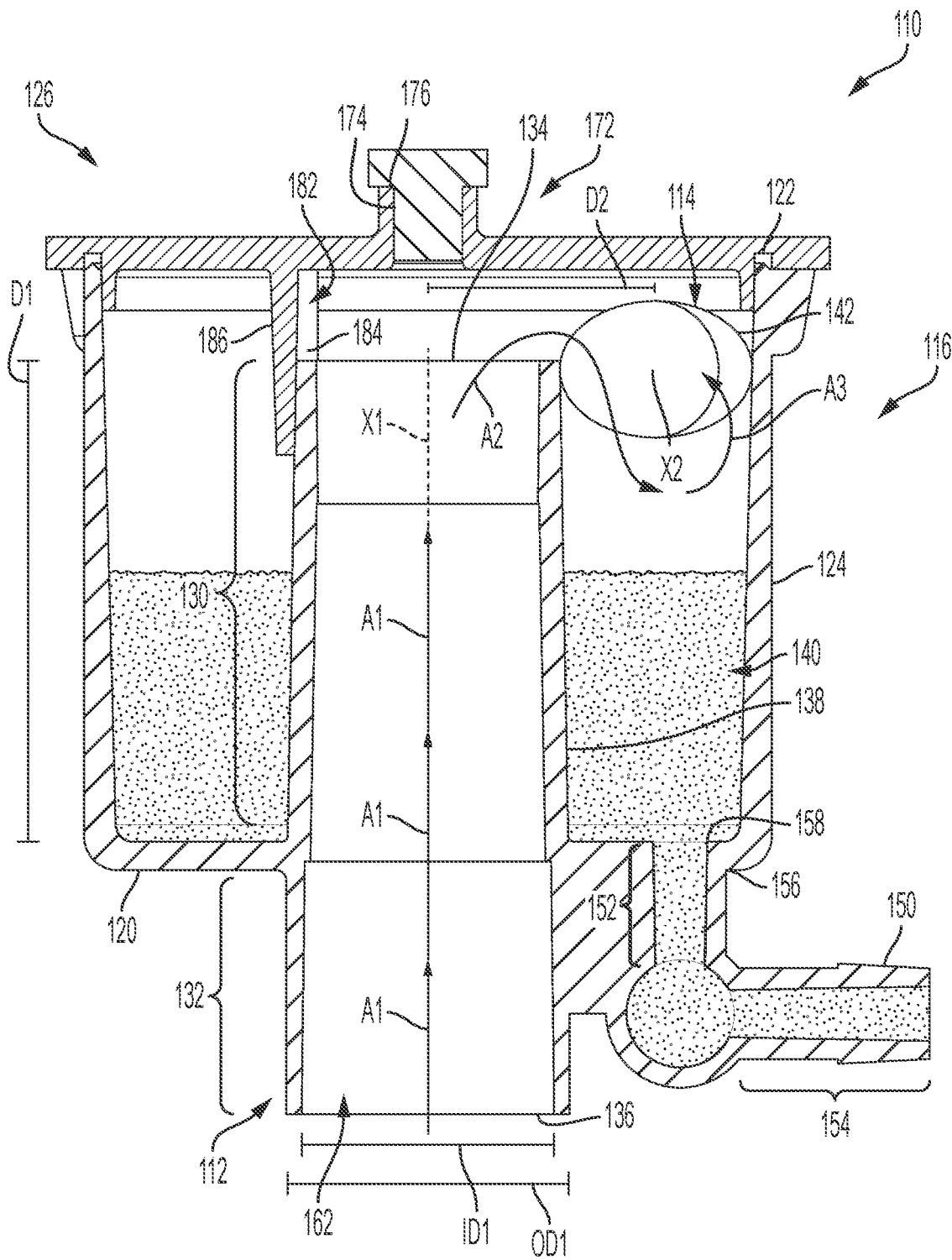
FIG. 2C is a cross-sectional view of the humidifier adaptor of FIG. 2A taken along line 2C-2C (in FIG. 2B)
Figure 2D:
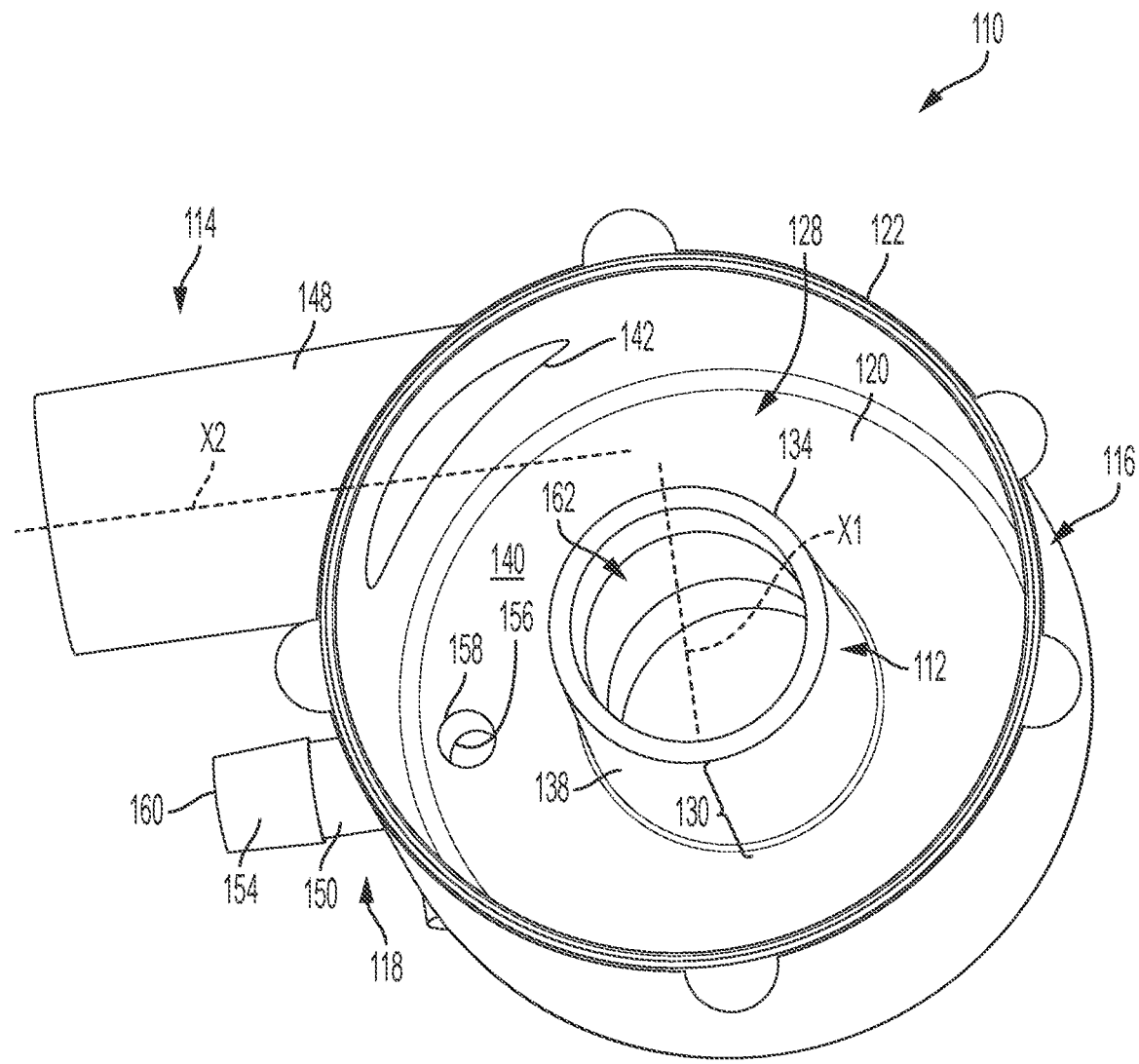
FIG. 2D is a top view of the humidifier adaptor of FIG. 2A, with the cap removed to show an interior of the humidifier adaptor.

The inlet 112 can be positioned to at least partially inhibit fluid and/or debris, which enters the chamber 128 through the outlet 114, from passing into the inlet 112 through the inner or second end 134 thereof. Fluids and/or debris passing into the inlet 112 may flow to the humidifier 18, thereby introducing contaminants to the humidifier 18. In order to prevent such back flow of fluid and/or debris, the sidewall 138 of the inlet 112 can extend above and/or be spaced apart from the base 120 of the housing 116 by, for example, a distance D1, thereby creating or defining a fluid collection portion or space 140 of the housing 116 below the inner or second end 134 of the inlet 112. The distance D1 can be, for example, between about 2.5 cm and 10 cm. Fluid and debris that enters the chamber 128 through the outlet 114 collects in the fluid collection space 140, as shown in FIG. 2C.

In some examples, the inlet 112 is sized to connect to the outflow port 26 of the humidifier 18. For example, as shown in FIGS. 5 and 6, the outflow port 26 of the humidifier 18 can be inserted into the inlet 112 through the external or first end 136 thereof. In order to form a suitable connection to the outflow port 26 of the humidifier 18, an inner diameter ID1 of the inlet 112 should be slightly larger than an outer diameter of the outflow port 26 of the humidifier 18. Since the outflow port 26 of the humidifier 18 is sized to be inserted into standard-sized medical tubing having an inner diameter of from about 10 mm to about 25 mm, or about 22 mm, the inner diameter ID1 of the inlet 112 is also from about 10 mm to 26 mm, or about 22.5 mm. The outer diameter OD1 of the inlet 112 can be from about 17 mm to 30 mm, or 25 mm. The sidewall 138 of the inlet 112 can be about 1 mm to 5 mm thick.

Figure 2E:
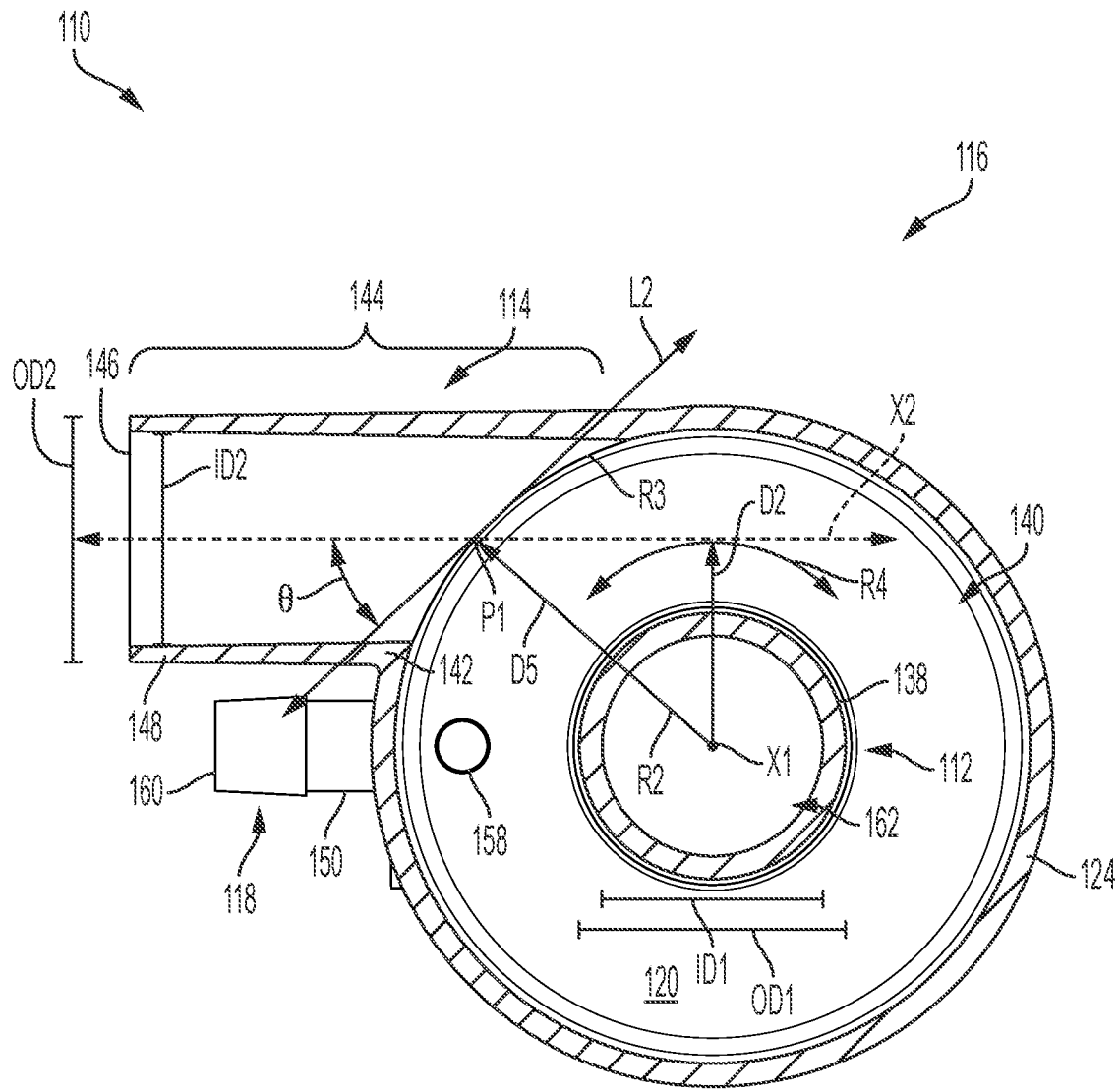
FIG. 2E is a cross-section view of the humidifier adaptor of FIG. 2A taken along line 2E-2E (in FIGS. 2A and 2B)

The humidifier adaptor 110 further comprises the outlet 114. The outlet 114 can be a tangential outlet in the sidewall 124 of the housing 116 configured such that air flows substantially tangentially out of the chamber 128 through the outlet 114. As used herein, a "tangential" outlet is an outlet which extends from the sidewall 124 of the housing 116 in a tangential direction. For example, as shown in FIG. 2E, the tangential outlet 114 can be configured such that a central axis X2 of the tangential outlet 114 is co-planar with and tangent to an arc R4 centered on a central axis X1 of the inlet 112. In some examples, the central axis X2 can be tangent to any co-planar arc centered on the central axis X1 of the inlet 112. Also, the central axis X1 of the inlet 112 can be generally perpendicular to the central axis X2 of the outlet 114. In some examples, the central axis X2 of the tangential outlet 114 can be offset by an angle θ. As shown in FIG. 2E and as used herein, the angle θ is defined as an angle between the central axis X2 of the tangential outlet 114 and a virtual line L2. The virtual line L2 is a line tangent to an arc, such as arc R3, defined by an inner surface of the sidewall 124 of the housing 116 at an intersection point P1 between the central axis X2 and the arc R3. In some examples, the angle θ is less than 90°. In some examples, the angle θ is from about 20° to about 70°. The tangential outlet 114 may also be positioned such that the central axis X2 of the outlet 114 does not follow and/or is not co-extensive with a radius R2 of the cylindrical housing 116 passing through the point P1.

In some examples, the tangential outlet 114 is spaced apart from the inlet 112, such that fluid and/or debris passing through the outlet 114 into the chamber 128 is at least partially inhibited from entering an interior portion 162 of the inlet 112. For example, the outlet 114 may be spaced apart from the inlet 112 by a distance D5 of at least 10 mm, or from 10 mm to 100 mm. As used herein, a flow of debris and/or fluid is "at least partially inhibited" from entering the inlet 112 when a substantial amount of fluid and/or debris passing into the chamber 128 is directed to the collection space 140 and does not pass into the inlet 112. For example, the outlet 114 can be positioned so that a volume of 60%, 70%, 80%, 90% or more of fluid and/or debris passing into the chamber 128 is directed to the collection space 140 and does not enter the interior portion 162 of the inlet 112.

In some examples, the inlet 112 can also be offset from the outlet 114. As shown in FIG. 2E, "offset" means that a longitudinal or central axis X1 of the inlet 112 is spaced apart from the longitudinal or central axis X2 of the outlet 114, such that the longitudinal or central axis X1 of the inlet 112 does not intersect the longitudinal or central axis X2 of the outlet 114 at any point along the axes X1, X2. In some examples, the longitudinal or central axis X1 can be spaced apart from the longitudinal or central axis X2 by a distance D2 of at least about 10 mm, or from about 10 mm to about 50 mm.

In some examples, the outlet 114 is a hollow member and/or tube comprising an end 142 in the sidewall 124 of the housing 116, an external portion 144 comprising an external end 146 configured to connect to the inspiratory tube 36 of the ventilator circuit or system 10, and a sidewall 148 extending therebetween. The sidewall 148 of the outlet 114 can be integrally formed with and protrude through the sidewall 124 of the housing 116. In other examples, the outlet 114 can be a separately molded or formed structure mounted to the sidewall 124 of the housing 116 in any convenient manner.

The outlet 114 can be sized so that the inspiratory tube 36 can be inserted over the external end 146 of the outlet 114, thereby connecting the inspiratory tube 36 to the humidifier adaptor 110. As discussed previously, conventional inspiratory tubes 36 used in ventilator circuits or systems 10 can have an inner diameter of about 10 mm to about 25 mm, or about 22 mm. In order to form a suitable connection with the inspiratory tube 36, the outlet 114 can have an outer diameter OD2 which is slightly smaller than the inner diameter of the inspiratory tube 36. For example, an outer diameter OD2 of the outlet 114 can be from about 9 mm to about 24 mm, or about 21 mm. An inner diameter ID2 of the outlet 114 can be about 6 mm to 22 mm, or about 18 mm. The sidewall 148 of the outlet 114 can be about 1 mm to 5 mm thick.

In some examples, the humidifier adaptor 110 further comprises the suction port or drain outlet 118 for removing the fluid and/or debris from the ventilator system 10 by evacuation through the chamber 128. The drain outlet 118 can be positioned in the base 120 of the housing 116. The drain outlet 118 can comprise a tube or connector 150 forming, for example, a right angle and comprising, for example, a vertical segment 152 and a horizontal segment 154. The connector 150 can further comprise an open inner end 156 inserted into and/or connected to an opening 158 in the base 120 of the housing 116. The angled connector 150 can further comprise an open external end 160 opposite the internal end 156 and a sidewall extending between the internal end 156 and the external end 160. The drain outlet 118 can be integrally formed with the base 120 of the housing 116. In other examples, the drain outlet 118 can be a separate tubular structure mounted to the opening 158 in the base 120 of the housing 116. For example, the drain outlet 118 may comprise a segment of flexible tubing connected to the opening 158 in the base 120 of the housing 116 by a suitable adhesive sufficient to seal the opening 158 to the housing 116.

In some examples, the open external end 160 of the connector 150 is configured to be connected to the suction source 12 for providing negative pressure to the chamber 128. For example, the external end 160 of the drain connector 150 may be sized to be inserted over a suction port or to be inserted into a suction hose to form a suitable connection therewith. In some examples, the external end 160 can be tapered and/or form a male portion of a luer connector to enhance the connection between the drain connector 150 and suction line or suction port. When suction is turned on, fluids and debris can pass from the chamber 128, through the drain outlet 118, and into the suction source 12.

The drain outlet 118 can further comprise a valve 164 positioned between the internal end 156 and the external end 160 of the connector 150. The valve 164 can be any suitable valve for preventing fluid flow from the housing 116 at undesirable or unintended times. In some examples, the valve 164 can be one or more of: a spring-loaded valve, a check valve, a solenoid valve, or other valve structures, as is known in the art. Generally, the valve 164 remains closed until the drain outlet 118 is connected to the suction source 12. Once the drain outlet 118 is connected to the suction source 12, the valve 164 can be manually or automatically opened to permit fluid in the chamber 128 to pass from the chamber 128 through the drain outlet 118.

Figure 3B:
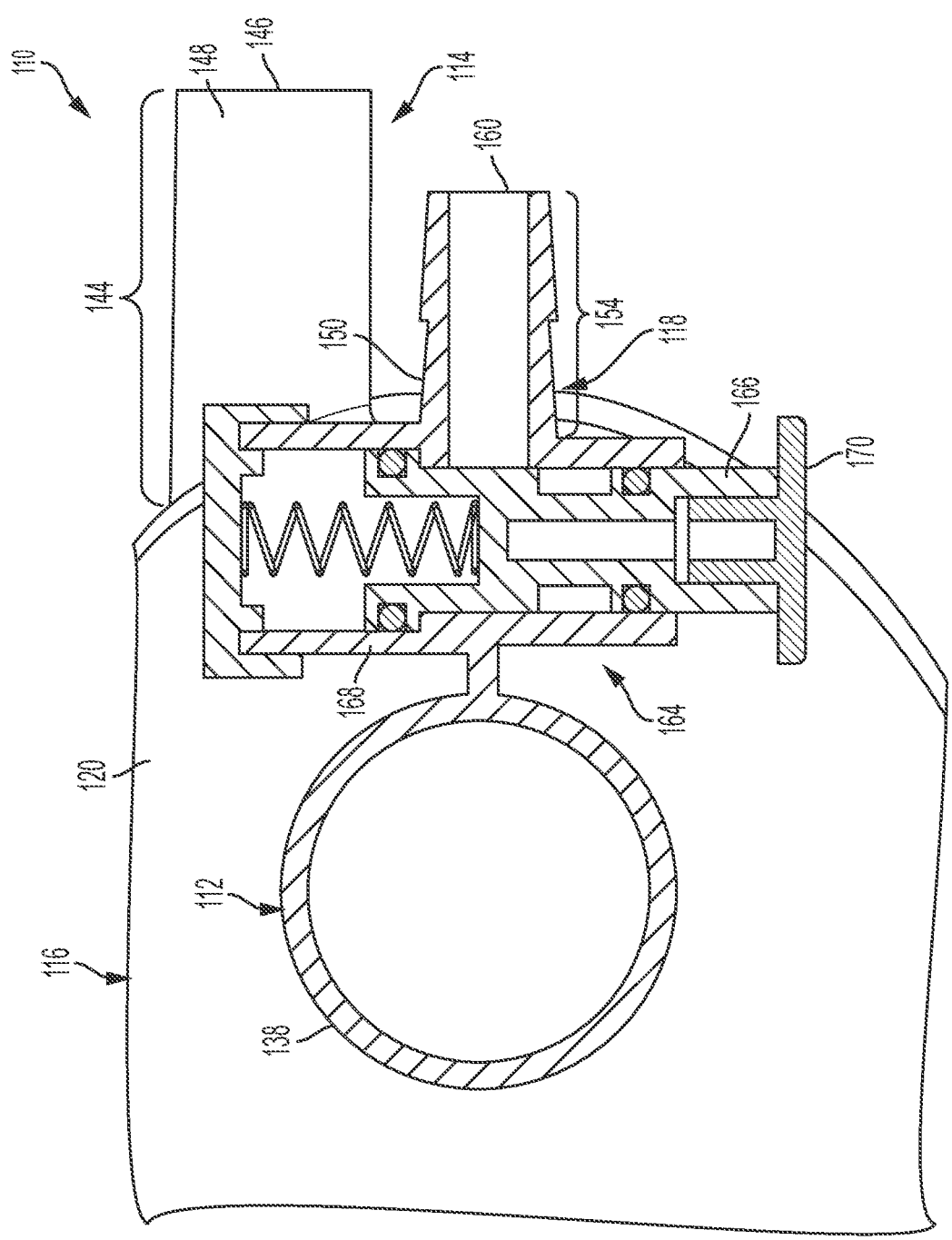
FIG. 3B is a cross-sectional view of the valve of the humidifier adaptor of FIG. 2A.

In some examples, as shown in FIGS. 3A and 3B, the valve 164 is a manually actuated spring-loaded valve comprising a piston 166 configured to be advanced into a valve body 168. The piston 166 can include a pressing surface 170 configured to be contacted by a user to advance the piston 166. For example, in order to transition the valve 164 from a closed position to an open position, the user can apply pressure to the pressing surface 170 to push the piston 166 into the valve body 168, thereby allowing fluid to pass through the valve 164. When the user stops applying pressure to the pressing surface 170, the piston 166 can automatically return to the closed position. This automatic closing can be a safety feature that prevents negative pressure from being applied to the circuit 10 for extended periods of time even if suction is left on by the user.

Figure 4A:
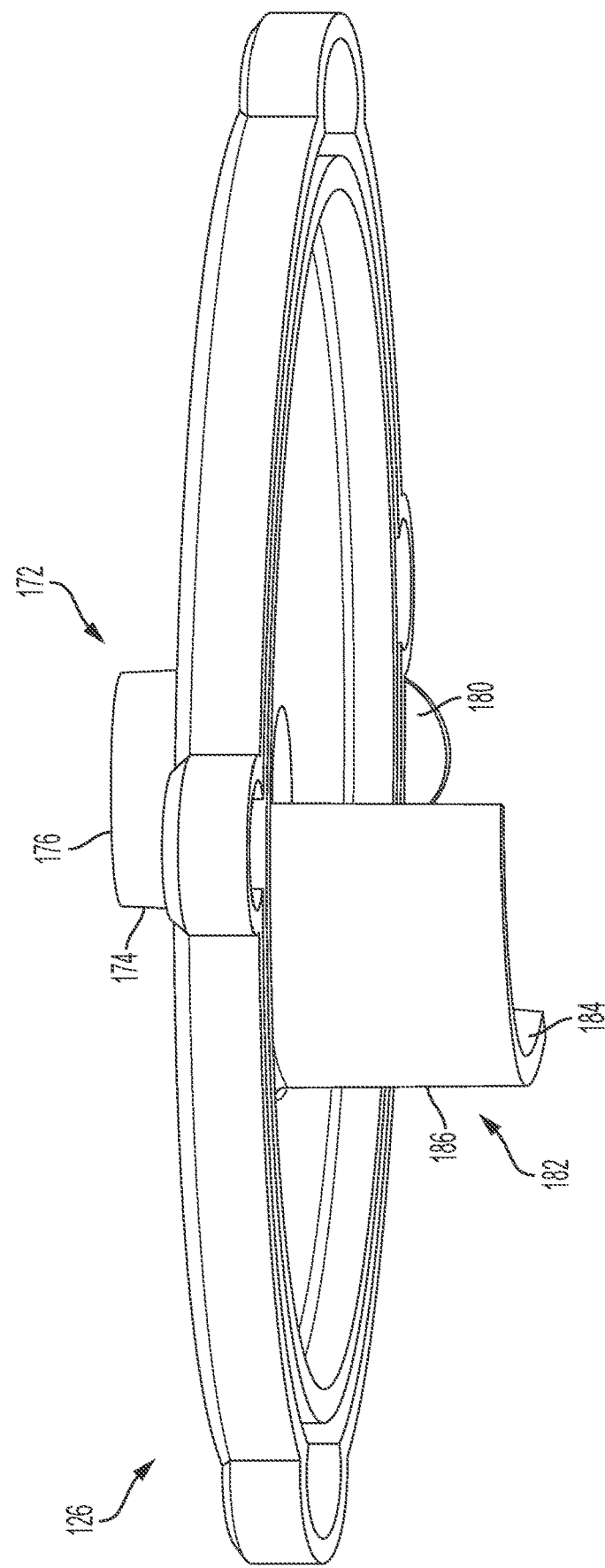
FIG. 4A is a perspective view of the cap of the humidifier adaptor of FIG. 2A, according to an example of the disclosure.
Figure 4B:
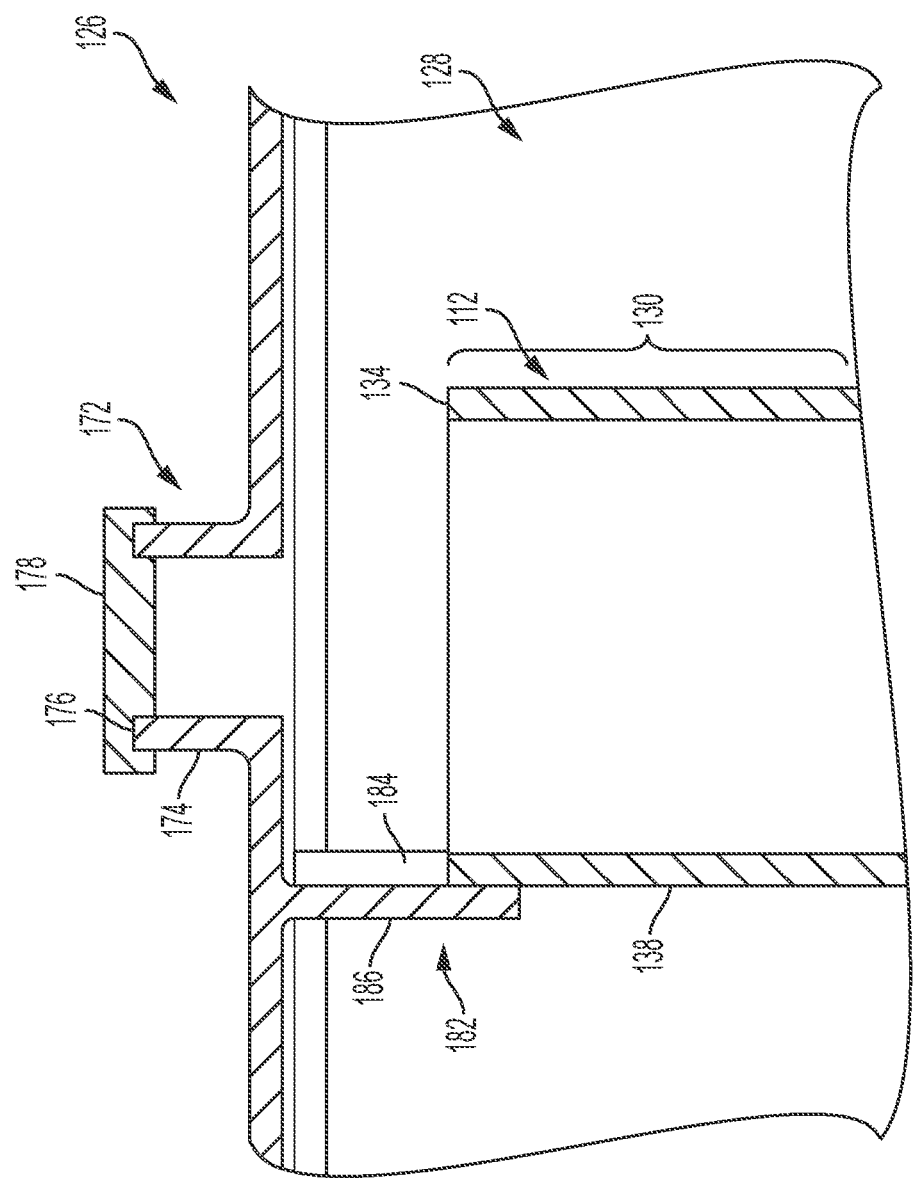
FIG. 4B is a cross-sectional view of a top portion of the humidifier adaptor of FIG. 2A, showing the cap and splash shield, according to an example of the disclosure.

With reference to FIGS. 4A and 4B, the humidifier adaptor 110 can further comprise the cap 126 removably or fixedly connected to the top 122 of the housing 116. For example, the cap 126 can be mounted to the sidewall 124 on the housing 116 by ultrasonic welding or adhesives, effectively permanently mounting the cap 126 to the housing 116. In other examples, the cap 126 may be removable. For example, the cap 126 may comprise screw threads (not shown) configured to engage corresponding threads (not shown) near the top 122 of the sidewall 124 of the housing 116 to removably mount the cap 126 to the housing 116.

In some examples, the cap 126 comprises a temperature opening or port 172 for receiving a temperature probe or temperature sensor 42 (shown in FIG. 1). For example, the temperature opening or port 172 can be a tapered structure comprising an annular body 174 defining a tapered cavity extending to an opening 176 in the cap 126. The temperature probe 42 can be mounted in place within the cavity, such that a sensory portion of the probe 42 extends into the chamber 128. Measurements from the temperature sensor or probe 42 can be used to ensure that ventilator airflow is a correct temperature to be delivered to the patient 14. For example, airflow should be about 37° C. when delivered to the patient 14. If measured temperature of the provided oxygenated airflow is not within an acceptable target range, operating parameters of the humidifier 18 and/or ventilator 16 can be manually or automatically adjusted to modify the temperature of air received in the chamber 128 from the humidifier 18. It is believed that measuring a temperature of air in the humidifier adaptor 110, which is located between the humidifier 18 and the patient 14, provides a reasonably accurate indication of a temperature of air being delivered to the patient 14. If the temperature port 172 were not present, air temperature could be measured either through another adaptor positioned between outflow port 26 of the humidifier 18 and the adaptor 110 or in the humidifier 18 through another access port. In that case, the target air temperature would need to be adjusted (possibly by about 5° C. to 10° C.) to account for heat loss, as the air passes through the humidifier 18, humidifier adaptor 110, and inspiratory tube 36. In other examples, temperature could be measured using another adaptor positioned between the outlet 114 of the humidifier adaptor 110 and the inspiratory tubing 36.

In some examples, the humidifier adaptor 110 further comprises a cover 178 (shown in FIG. 4B), such as a stretchable and/or elastomeric cover, configured to be placed over the temperature sensor port 172 when the temperature probe 42 is not being used. The cover 178 can be a plug sized to be partially inserted into the port 172 to seal or partially seal the port 172 when the temperature probe 42 is not being used. The cover 178 can be connected to the cap 126 or another portion of the humidifier adaptor 110 by a tether (not shown) or another connector, to avoid losing the cover 178, and to ensure that the cover 178 is easily available when needed. In some examples, the cap 126 can comprise a protrusion or lug 180 for attaching the tether to the cap 126.

Figure 4C:
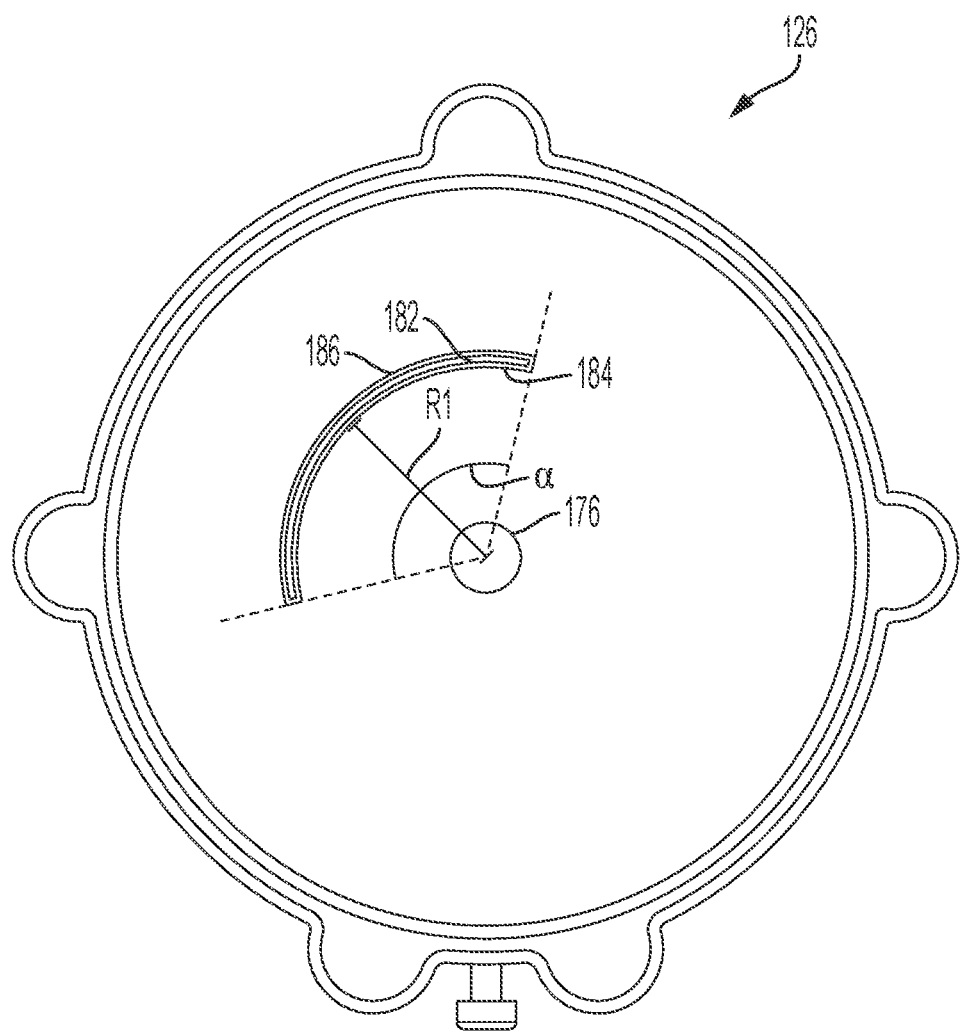
FIG. 4C is a bottom view of the cap of FIG. 4A.

In some examples, the humidifier adaptor 110 further comprises a splash shield 182 extending from an inner surface of the cap 126 into the chamber 128. The splash shield 182 is configured to protect the inner or second end 134 of the inlet 112 and, in particular, to prevent fluids collecting in the base 120 of the housing 116 from splashing towards the inner or second end 134 and passing into the inlet 112. As discussed previously, backflow of fluids through the inlet 112 into the humidifier 18 should be avoided to prevent contamination of the humidifier 18. In some examples, the splash shield 182 comprises an arcuate structure comprising a curved inner surface 184 and opposing curved outer surface 186. For example, as shown in FIG. 4C, the splash shield 182 can comprise a curve having a radius R1 of from about 8 mm to about 14 mm, or about 12 mm. The splash shield 182 can define a curve of about 60° to about 180°, or about 120°, as shown by angle α (shown in FIG. 4C). As shown in FIG. 4B, the splash shield 182 may have a curvature configured to match a curvature of the inlet 112. For example, the inner surface 184 of the shield 182 can contact an outer surface of the sidewall 138 of the inlet 112, thereby surrounding a portion of the inner or second end 134 of the inlet 112. By partially surrounding the inner or second end 134 of the inlet 112, the shield 182 reduces or prevents fluids in the housing 116 from splashing into the interior portion 162 of the inlet 112, thereby providing additional protection against backflow of fluid into the humidifier 18.

Method of Removing Secretion Fluids from a Ventilator System

Having described the ventilator circuit or system 10 and humidifier adaptor 110, a method for removing fluids and/or debris from a ventilator circuit or system 10 will now be described. The method is generally practiced by a respiratory therapist or similarly skilled medical professional during ventilation of a patient 14. As described previously, the method is intended to be performed without disconnecting the ventilator circuit or system 10 from the patient 14. Fluids and/or debris can be removed from the ventilator circuit or system 10 as needed or at periodic intervals.

Figure 7:
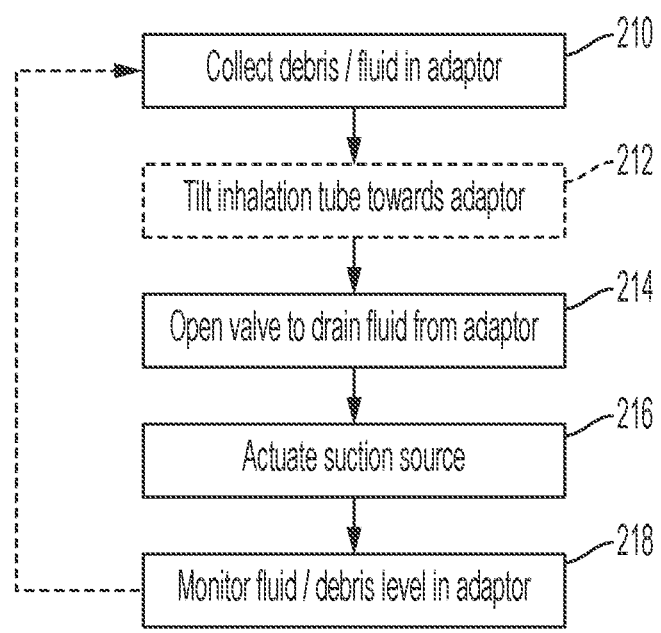
FIG. 7 is a flow chart showing a method for removing secretions from a ventilator system, according to an example of the disclosure.

With reference to FIG. 7, at step 210, the method for removing debris and fluids from the ventilator circuit or system 10 comprises collecting debris and fluid from the inspiratory tube 36 of the ventilator circuit or system 10 in the humidifier adaptor 110. For example, the debris and fluid may pass through the tube 36 and into the adaptor 110 by gravity. Optionally, as shown at step 212, in order to enhance flow, the user can tilt the inspiratory tube 36 towards the humidifier adaptor 110. For example, the user may grasp the inspiratory tube 36 and raise or adjust a position of the tube 36 so that the debris and fluids flow through the tube 36 away from the patient 14 and towards the humidifier adaptor 110. In some examples, the user can tilt the tube 36 towards the humidifier adaptor 110 for a few seconds and then release the tube 36. After the tube 36 is released, fluid and debris can continue to flow into the adaptor 110 by gravity. The debris and fluids can collect in the fluid collection space 140 near the base 120 of the housing 116. Desirably, a level of fluid in the housing 116 remains far below the internal or second end 134 of the inlet 112 to prevent backflow of fluids through the inlet 112 into the humidifier 18.

At step 214, the user can open the valve 164 of the drain outlet 118 to begin draining the fluids and/or debris out of the chamber 128. For example, as discussed previously, the user may press on the pressing surface 170 of the valve piston 166 causing the piston 166 to move to the open position. Once the valve 164 is in the open position, the debris and/or fluid from the humidifier adaptor 110 can flow through the drain outlet 118 and away from the ventilator circuit or system 10 by gravity.

At step 216, in order to enhance drainage from the chamber 128 and inspiratory tube 36, the user can actuate the suction source 12, such as a suction line or vacuum pump, to apply negative pressure to the chamber 128 through the drain outlet 118. Negative pressure can be applied until the chamber 128 appears to be empty. Once the chamber 128 appears to be empty, the user can turn off the suction source 12 to stop applying the negative pressure to the chamber 128 and/or can release the pressing surface 170 of the piston 166 so that the valve 164 returns to its closed position. In some examples, the suction source 12 can remain on for an extended period or all of the time. In that case, the user can periodically open the valve 164 for short periods (e.g., for a few seconds) to draw fluid and debris from the adaptor 110 under suction. As discussed previously, the valve 164 automatically closes when the pressing surface 170 of the piston 166 is released by the user.

After turning off the suction and/or releasing the valve 164, at step 218, the user may continue to monitor an amount of fluid and/or debris in the inspiratory tube 36 and/or in other portions of the ventilator circuit or system 10. The user can repeat the steps for removing fluids and/or debris from the tubing as needed to ensure that the patient 14 continues to receive oxygenated air and to prevent portions of the ventilator circuit or system 10 from being occluded by fluids or debris.

Method of Assembling a Ventilator Circuit

Figure 8:
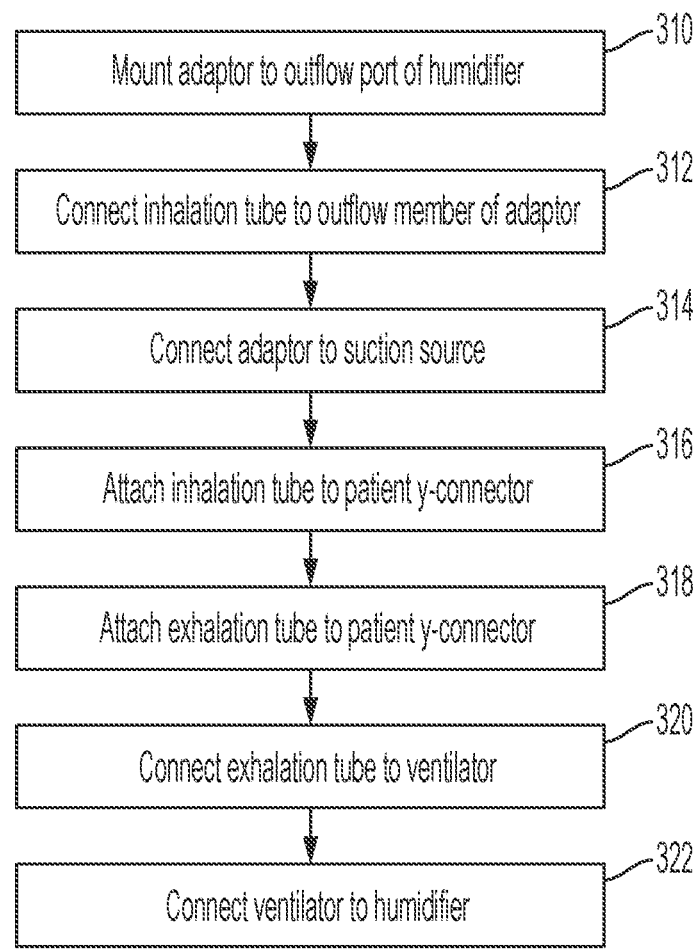
FIG. 8 is a flow chart showing a method for assembling a ventilator system, according to an example of the disclosure.

According to another example of the disclosure, a method for assembling a ventilator circuit or system 10 is shown in FIG. 8. As shown in FIG. 8, the method comprises, at step 310, mounting the humidifier adaptor 110 to the outflow port 26 of the humidifier 18. As described previously, mounting the humidifier adaptor 110 to the humidifier 18 can comprise pressing the external or first end 136 of the inlet 112 over the outflow port 26 of the humidifier 18 to establish fluid communication between the humidifier 18 and the chamber 128. In some examples, the outflow port 26 of the humidifier 18 or the inlet 112 can include structures for enhancing a seal between the outflow port 26 and the inlet 112. For example, either an outer surface of the outflow port 26 or the inner surface of the inlet 112 can comprise protrusions, ridges, rings, or other structural features for securing the outflow port 26 and inlet 112 together. In other examples, the inlet 112 and/or outflow port 26 can comprise tapered portions, luer connecting structures, or similar structural features for securing the humidifier adaptor 110 to the humidifier 18.

At step 312, the method further comprises connecting an end of an inspiratory tube 36 to the outlet 114 of the humidifier adaptor 110. For example, the outlet 114 of the humidifier adaptor 110 can be inserted into the end of the inspiratory tube 36 to form a suitable connection between the inspiratory tube 36 and humidifier adaptor 110. The outlet 114 and/or inspiratory tube 36 can include structures for enhancing the seal and connection between the outlet 114 and the inspiratory tube 36. For example, an outer surface of the outlet 114 can include ridges or protrusions for securing the outlet 114 to the inspiration tube 36. In some examples, the outlet 114 can be shaped like a luer connector forming a secure connection to the inspiratory tube 36.

At step 314, optionally, the method further comprises attaching the humidifier adaptor 110 to the suction source 12. For example, the open external end 160 of the drain connector 150 can be connected to a suction line or suction port. As discussed previously, debris and fluids can be removed from the humidifier adaptor 110 under suction through the drain connector 150. Alternatively, as previously described, fluids and debris can be drained from the adaptor 110 by gravity. In that case, no suction source 12 is needed for the circuit 10.

At step 316, the method further comprises attaching an opposing end of the inspiratory tube 36 to the y-connector 30. For example, the inspiratory tube 36 can be inserted onto the inflow port 34 of the y-connector 30. As discussed previously, the opposing patient-side port 32 of the y-connector 30 is connected to the patient 14 through the interface assembly 28, such as an endotracheal tube, nasal cannula, or breathing mask.

At step 318, the method further comprises attaching the expiratory tube 40 to the outflow port 38 of the y-connector 30. For example, the outflow port 38 of the y-connector 30 can be inserted into an open end of the expiratory tube 40 to form a suitable connection with the y-connector 30, and to establish fluid communication from the patient's airway, through the y-connector 30, to the expiratory tube 40. At step 320, the expiratory tube 40 can be connected to an inflow port of a ventilator 16 for returning exhaled air to the ventilator 16.

At step 322, an outflow port of the ventilator 16 can be connected to the humidifier 18 (e.g., at the humidifier inflow port 20) through additional lengths of tubing 22, thereby forming the ventilator circuit or system 10. Once the ventilator circuit or system 10 is formed, airflow generated by the ventilator 16 can pass from the ventilator 16 through the outflow port and tubing 22 to the humidifier 18. In the humidifier 18, oxygenated air from the ventilator 16 is heated and absorbs moisture. The oxygenated and humidified air is then expelled from the humidifier 18 into the humidifier adaptor 110. The oxygenated and humidified air then flows through the humidifier adaptor 110 and to the patient 14 through the inspiratory tube 36, y-connector 30, and patient interface assembly 28. Fluids and/or debris in the ventilator circuit or system 10 can be collected in the humidifier adaptor 110 and removed from the ventilator circuit or system 10 through the drain outlet 118 under suction and/or by gravity, as previously described. Exhaled air passes through the patient interface assembly 28, y-connector 30, and expiratory tube 40 back to the ventilator 16.

Fluid Circuit for Y-Connector Adaptor

Figure 9:
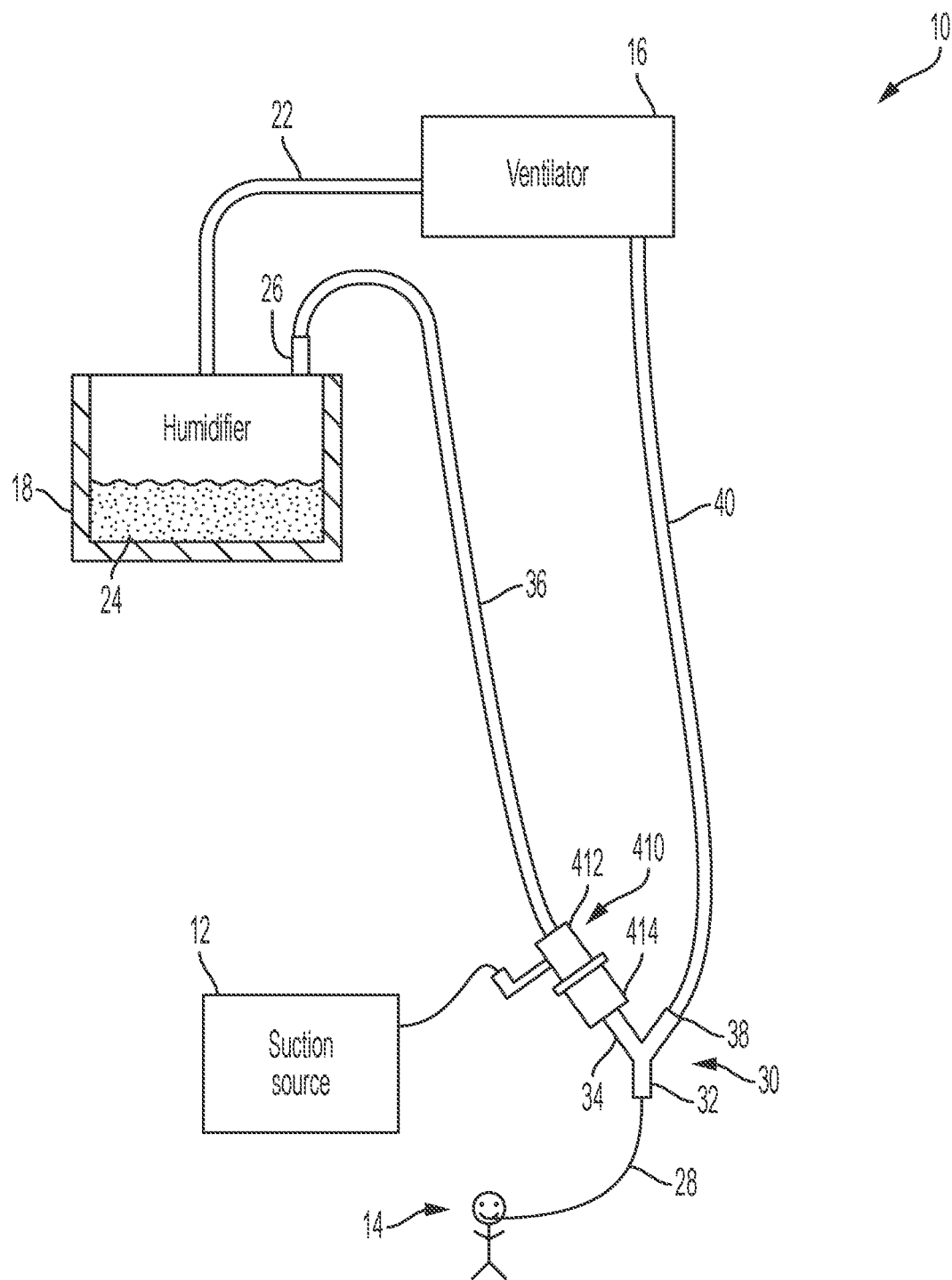
FIG. 9 is a schematic drawing of another example of a ventilator system including an adaptor configured to be connected to a y-connector of a ventilator system, according to an example of the disclosure.

FIG. 9 shows another example of a ventilator circuit or system 10 including a y-connector adaptor 410 for removing fluids and/or debris from tubing (e.g., the inspiratory tube 36 and/or expiratory tube 40) of the ventilator circuit or system 10. As in previous examples, the ventilator circuit or system 10, shown in FIG. 9, can comprise the inspiratory tube 36, the expiratory tube 40, the ventilator 16, and the humidifier 18. The ventilator circuit or system 10 also includes the y-connector 30. The y-connector 30 includes the inflow port 34 connected to the inspiratory tube 36, the outflow port 38 connected to the expiratory tube 40, and the patient-side port 32 connected to the patient interface assembly 28, which is connected to the patient 14. As in previous examples, the patient interface assembly 28 can comprise, for example, an endotracheal tube, a nasotracheal tube, or a tracheal tube. In other examples, the patient interface assembly 28 can comprise a nasal cannula, breathing facemask, or similar structure for delivering oxygenated air to the patient 14. Unlike in previous examples, in which the humidifier adaptor was mounted to the humidifier 18, as shown in FIG. 9, the ventilator circuit or system 10 comprises the y-connector adaptor 410 connected to the inspiratory side of the y-connector 30. The y-connector adaptor 410 can comprise an inflow side 412 and an outflow side 414. The outflow side 414 can be directly connected to the inflow port 34 of the y-connector 30. The inflow side 412 can be directly connected to an end of the inspiratory tube 36. An opposing end of the inspiratory tube 36 is connected directly or indirectly to the outflow port 26 of the humidifier 18.

The y-connector adaptor 410 can comprise a drain 418 configured to be connected to a suction source 12 for removing debris and fluids from the y-connector adaptor 410 and ventilator circuit or system 10. In some examples, debris and fluid can drain from the circuit 10 by gravity. To increase flow towards the adaptor 410, the user can tilt the inspiratory tube 36 towards the y-connector adaptor 410 and y-connector 30, thereby causing fluid and debris to flow from the inspiratory tube 36 into the adaptor 410. Also, as described in connection with the adaptor 110, negative pressure can be applied to the y-connector adaptor 410 to enhance removal of the collected debris and fluids from the ventilator circuit or system 10.

Y-Connector Adaptor

Figure 10A:
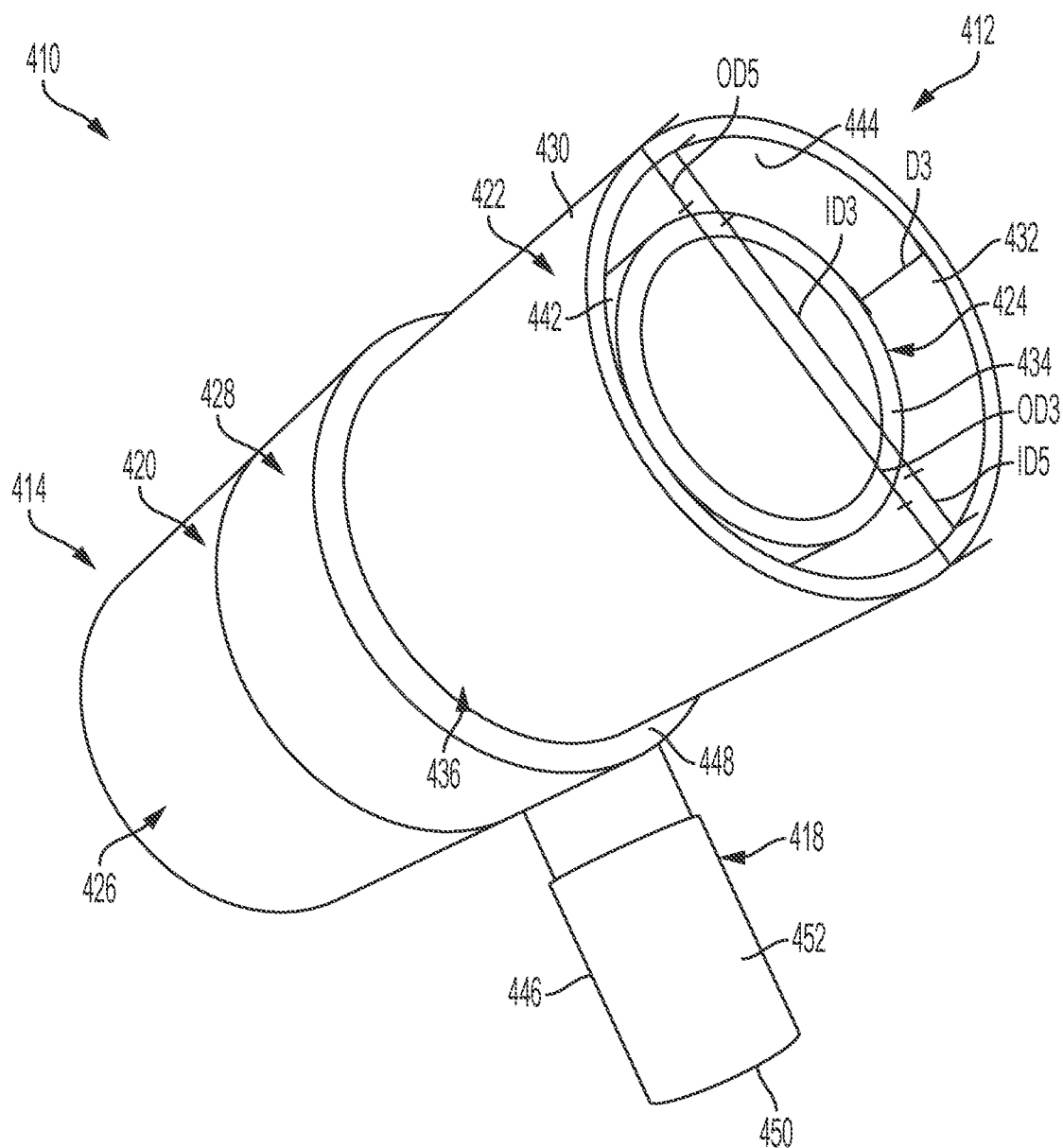
FIG. 10A is a perspective view the adaptor configured to be connected to a y-connector of a ventilator system, according to an example of the disclosure.
Figure 10B:
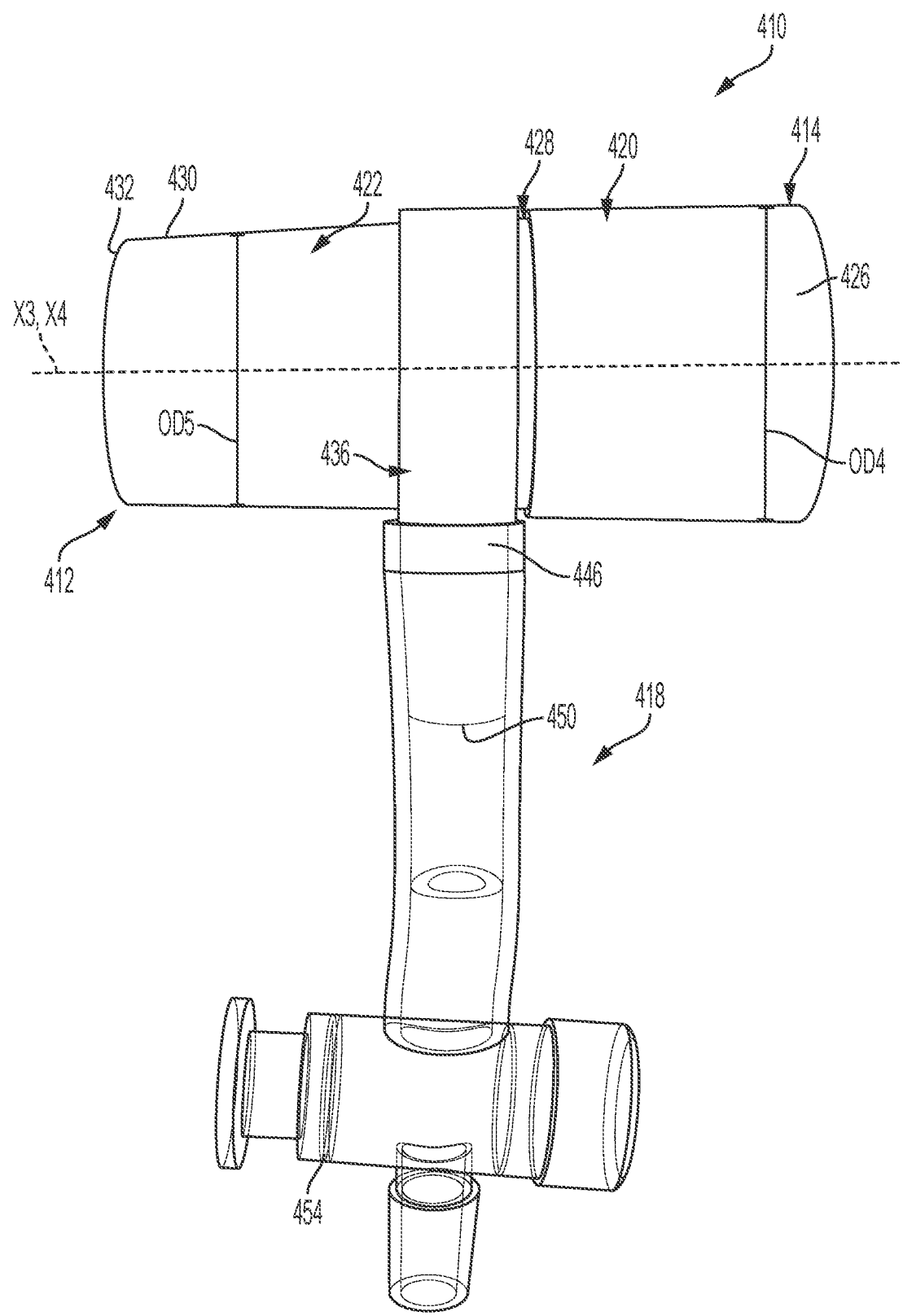
FIG. 10B is a front view of the adaptor of FIG. 10A.
Figure 10C:
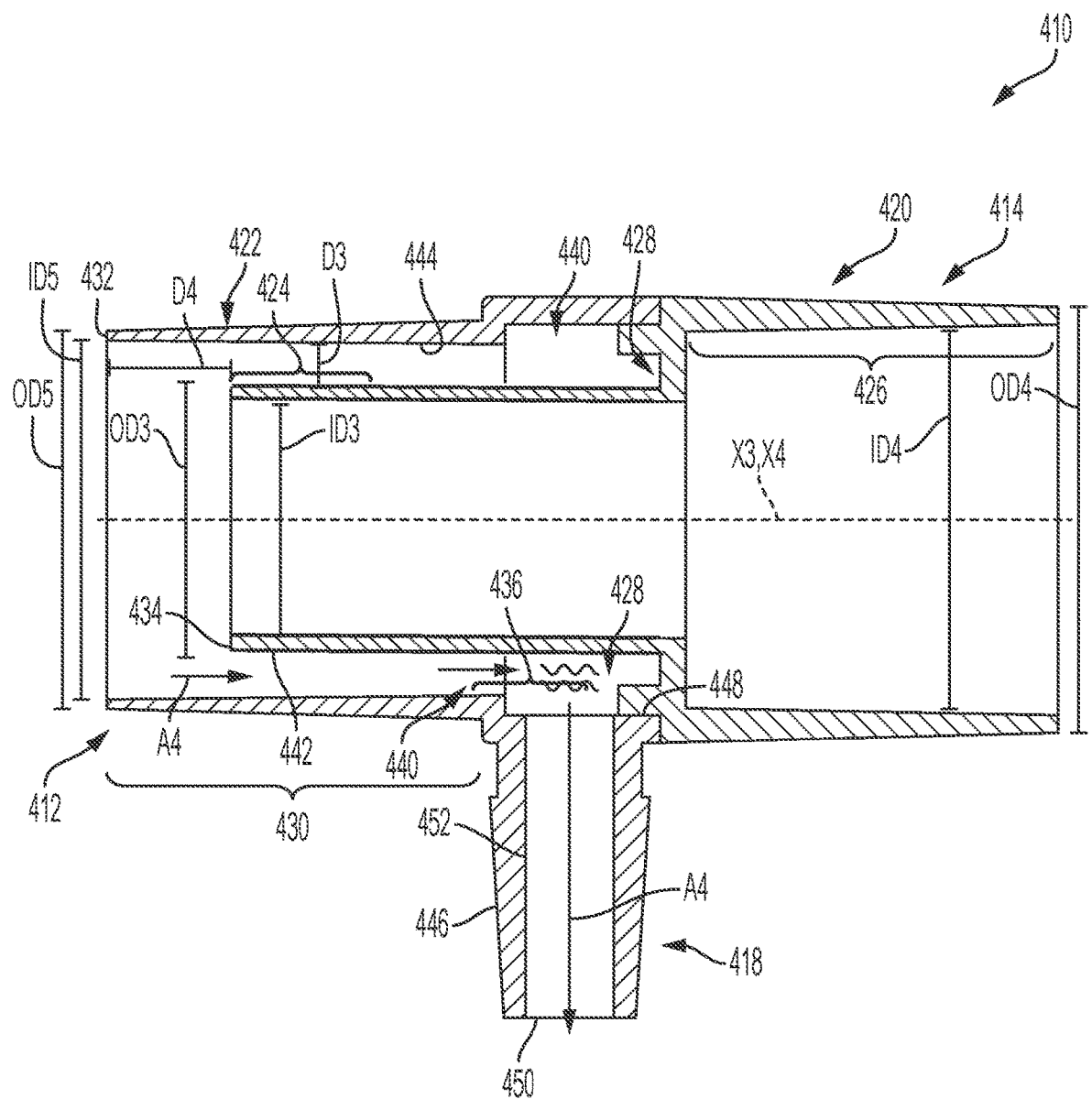
FIG. 10C is a cross-sectional view of the adaptor of FIG. 10A taken along line 10C-10C (in FIG. 10D)

With reference to FIGS. 10A-10D, features of the y-connector adaptor 410 will be described in further detail. The y-connector adaptor 410 comprises concentric or coaxial tubular housings, such as a first tubular housing 420 and a second tubular housing 422. As shown in FIG. 10C, the first tubular housing 420 can be partially inserted into and fixedly connected to the second tubular housing 422. As used herein, "concentric" or "coaxial" refers to tubular structures arranged along a common central axis. For example, the central axis X3 of the first tubular housing 420 can be co-extensive with the central axis X4 of the second tubular housing 422. The y-connector adaptor 410 can have a longitudinal length of about 2 cm to about 8 cm, or about 6 cm. As described in further detail herein, a diameter of the y-connector adaptor 410 varies along a length of the y-connector adaptor 410, and can be about 8 mm to 30 mm.

The tubular housings 420, 422 can be formed from rigid plastic materials, such as high density polyethylene, polyethylene terephthalate, polyvinylchloride, polycarbonates, and similar materials. The first housing 420 and the second housing 422 are generally fixedly connected together. In some examples, the housings 420, 422 can be integrally formed or molded thereby forming a unitary structure. However, due to a shape and dimensions of the housings 420, 422, simultaneously forming the housings by standard molding processes may be difficult. Accordingly, in some examples, the first housing 420 and the second housing 422 can be molded separately and fixedly connected together by, for example, ultrasonic welding, screw threads, solvent bonding, or a tapered press fit connection. The housings 420, 422 can also be connected together using other types of adhesives, fasteners, or other suitable connection techniques, as are known in the art.

In some examples, the first tubular housing 420 comprises an inflow portion (referred to herein as a first inflow portion 424), an outflow portion 426, and a shoulder portion 428 between the first inflow portion 424 and the outflow portion 426. The first inflow portion 424, the shoulder portion 428, and the outflow portion 426 can be axially aligned along the axis X3. The first inflow portion 424 and outflow portion 426 can comprise tubular segments having different diameters. For example, the first inflow portion 424 can have an outer diameter OD3 from about 10 mm to about 20 mm, or about 15 mm, and an inner diameter ID3 from about 8 mm to 18 mm, or about 13 mm. The outflow portion 426 can be sized to receive the inflow port 34 of the y-connector 30. Accordingly, an inner diameter ID4 of the outflow portion 426 can be slightly larger than conventional tubing and ports of the y-connector 30. For example, the inner diameter ID4 can be from about 10 mm to about 25 mm, or about 22 mm. An outer diameter OD4 of the outflow portion 426 can be about 12 mm to about 30 mm, or about 25 mm.

Figure 10D:
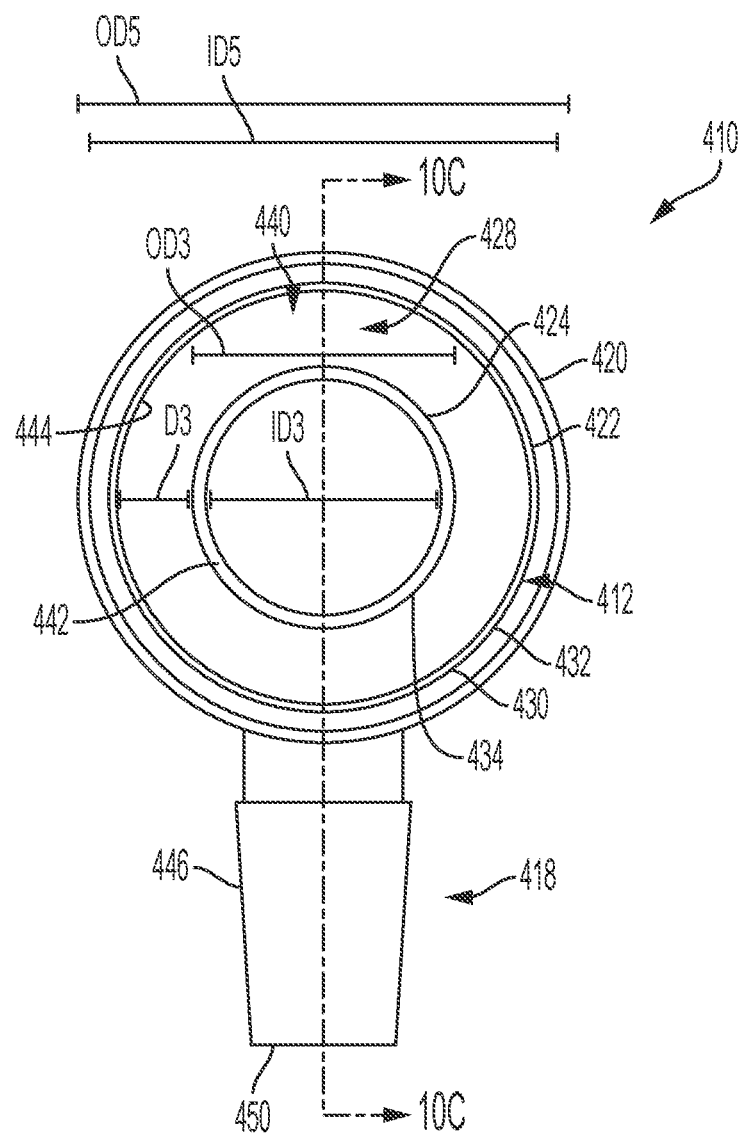
FIG. 10D is a right side view showing the inflow portion of the adaptor of FIG. 10A.

In some examples, the second tubular housing 422 extends circumferentially around at least a portion of the first inflow portion 424 of the first tubular housing 420 as shown, for example, in FIGS. 10A, 10C, and 10D. For example, at least a portion of the second tubular housing 422 can be connected to and/or integrally formed with the shoulder portion 428 of the first tubular housing 420. The second tubular housing 422 can comprise an inflow portion (referred to herein as a second inflow portion 430) comprising, for example, an open end 432 configured to connect to and receive oxygenated and humidified air from the inspiratory tube 36. In order to connect to a standard sized inspiratory tube 36, the second inflow portion 430 can have an outer diameter OD5 of about 10 mm to about 25 mm, or about 22 mm. An inner diameter ID5 of the second inflow portion 430 can be about 8 mm to about 22 mm, or about 20 mm.

In some examples, the second inflow portion 430 is spaced apart from the first inflow portion 424 by a radial distance D3 of about 1.5 mm to about 3.0 mm, or about 2.25 mm. In some examples, ends of the first inflow portion 424 and second inflow portion 430 of the housings 420, 422 can be substantially aligned. In other examples, an end 434 of the first inflow portion 424 can be recessed relative to the end 432 of the second inflow portion 430. For example, the end 432 of the second inflow portion 430 may extend beyond an end 434 of the first inflow portion 424 by a distance D4. The distance D4 can range from about 2.0 mm to about 5.0 mm, or about 2.5 mm. Recessing the first inflow portion 424 relative to the second inflow portion 430 can help to at least partially inhibit fluids from passing through the y-connector adaptor 410 to the y-connector 30 and patient 14.

In some examples, the second tubular housing 422 further comprises a drainage end or drainage portion 436 and a tubular sidewall extending between the second inflow portion 430 and the drainage portion 436. As discussed previously, the second tubular housing 422 further comprises the drain 418 extending through the drainage portion 436 of the second tubular housing 422 for removing the fluids and/or debris from the y-connector adaptor 410 when negative pressure is applied to the adaptor 410.

The first tubular housing 420 and the second tubular housing 422 provide or define a space 440 (shown in FIG. 10C) for collecting debris and fluids until the fluids can be removed through the drain 418. The fluid collection space 440 can be sized to hold a volume of fluids and/or debris of at least 3 mL, or of about 3 mL to about 5 mL. In some examples, the space 440 is located between an outer surface 442 of the first inflow portion 424, an inner surface 444 of the second inflow portion 430 of the second tubular housing 422, and the shoulder portion 428 of the first tubular housing 420.

In some examples, the drain 418 comprises an elongated hollow drain member or tube 446. The drain member or tube 446 can be integrally formed with other portions of the y-connector adaptor 410. Alternatively, the drain tube 446 can be a separate structure, such as flexible tubing, connected to and extending from the drainage portion 436 of the second tubular housing 422. The hollow drain member or tube 446 can comprise an open first end 448 integrally formed with or connected to the drainage portion 436, an open second end 450 opposite the first end 448, and a sidewall 452 extending therebetween. The drain tube 446 can define or provide a drainage fluid path for moving fluid in the fluid collection space 440 away from the y-connector adaptor 410. As in previous examples, the second end 450 of the drain tube 446 can be configured to be connected to the suction source 12, such as a suction line at a medical facility or a vacuum pump. When actuated, suction from the suction source 12 draws fluids in the fluid collection space 440 of the y-connector adaptor 410 through the drain 418 and away from the y-connector adaptor 410.

In some examples, the drain 418 further comprises a valve 454 (shown in FIG. 10B). The valve 454 can be removably or non-removably attached to the drain tube 446. For example, portions of the valve 454 can be integral with the drain tube 446. Alternatively, the valve 454 can be a separate structure connected to, for example, the second end 450 of the drain tube 446. The valve 454 can be configured to transition between a closed position, in which fluid flow from the fluid space 440 of the y-connector adaptor 410 is prevented, and an open position, in which fluid flow is permitted. The transition between open and closed can occur automatically or in response to an action by the user. For example, the valve 454 can be a manually actuated valve, such as a valve including a piston (not shown) that can be pressed and released by the user. In other examples, the valve 454 can be an automatic valve which, for example, automatically opens when suction is provided to the drain 418 from a suction source 12 and can be automatically closed once suction is stopped.

Secretion Fluid Removal Methods

Figure 11:
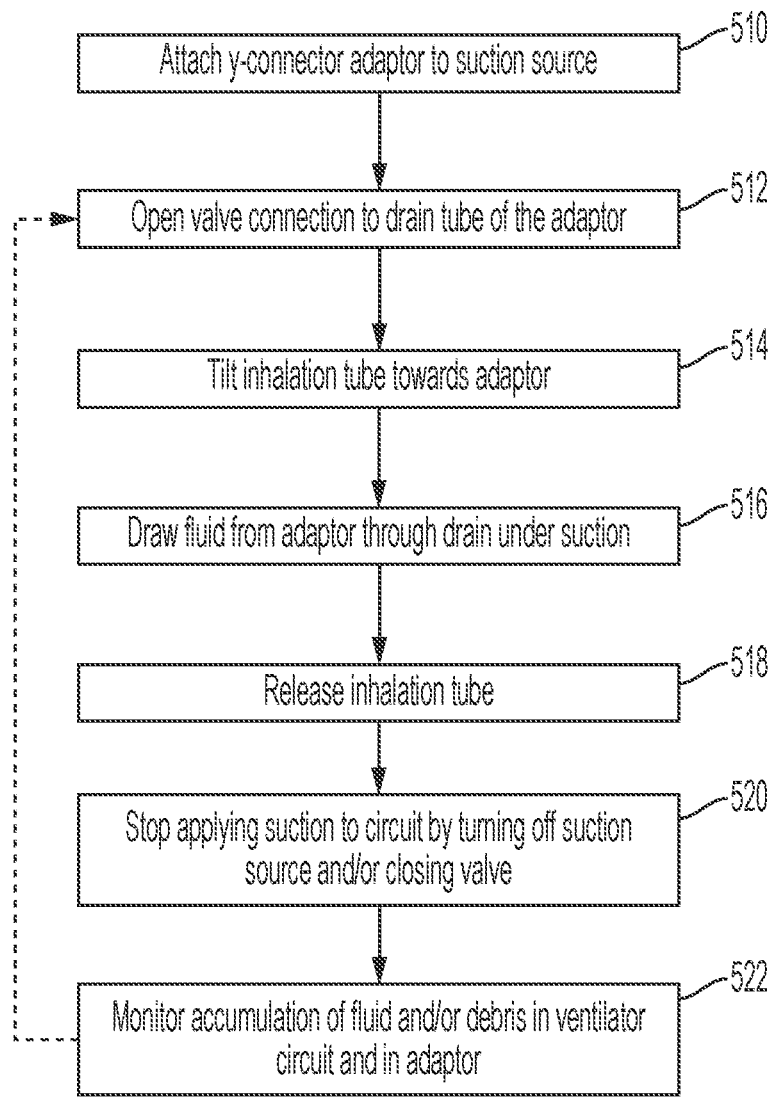
FIG. 11 is a flow chart showing another method for removing secretions from a ventilator system according to an example of the disclosure.

A method for removing debris and fluids from the ventilator circuit or system 10 using the y-connector adaptor 410 will now be described in detail. A flow chart showing steps for fluid removal through the y-connector adaptor 410 is shown in FIG. 11.

At step 510, the method initially comprises attaching the suction source 12, such as a suction line or vacuum pump, to the drain tube 446 extending from the y-connector adaptor 410. For example, the external or second end 450 of the drain tube 446 may be connected to a suction port or tube connected to the suction source 12 or pump. At step 512, in order to apply negative pressure to the y-connector adaptor 410, the user may open the valve 454 in the drain tube 446 by, for example, pressing on the piston, thereby causing the valve 454 to move to the open position.

At step 514, as negative pressure is applied to the y-connector adaptor 410, the user tilts the inspiratory tube 36 of the ventilator circuit or system 10 towards the y-connector adaptor 410. For example, the user may grasp the inspiratory tube 36 and raise it above the y-connector adaptor 410 so that debris and/or fluid in the inspiratory tube 36 flows through the tube 36 towards the y-connector adaptor 410. Due to the negative pressure applied to the interior of the y-connector adaptor 410, debris and/or fluid flows from the inspiratory tube 36 into the fluid collection space 440 between the first housing 420 and the second housing 422, as shown by arrow A4 in FIG. 10C. Desirably, fluid flowing into the y-connector adaptor 410 from the inspiratory tube 36 does not pass through the first inflow portion 424 and into the y-connector 30 and/or patient interface assembly 28. At step 516, due to the negative pressure applied to the y-connector adaptor 410, the debris and/or fluid in the fluid collection space 440 passes into the drain tube 446 and away from the y-connector adaptor 410.

Once a sufficient amount of debris and/or volume of fluid has been removed from the y-connector adaptor 410 and/or ventilator circuit or system 10, at step 518, the user releases the inspiratory tube 36 allowing it to fall back to a natural position in which, preferably, fluid in the inspiratory tube 36 does not flow towards the y-connector adaptor 410 and patient 14.

At step 520, the user can stop applying negative pressure by, for example, closing the valve 454 and/or turning off or disconnecting the suction source 12 or vacuum pump from the drain 418. The user can monitor the ventilator circuit or system 10 to determine when debris and fluids begin to collect in the inspiratory tube 36. The user can repeat the steps for removing the debris and fluids as needed or periodically according to a predetermined schedule or patient care protocol.

The preceding examples and embodiments of the invention have been described with reference to various examples. Modifications and alterations will occur to others upon reading and understanding the foregoing examples. Accordingly, the foregoing examples are not to be construed as limiting the disclosure.

What is claimed is:

1. A humidifier adaptor for evacuating fluid and/or debris from a ventilator system, comprising:
   (a) a housing comprising a base, a top, and at least one sidewall extending therebetween, which together define a chamber;
   (b) an inlet in the base of the housing extending into the chamber, the inlet comprising a first end configured to receive air from a humidifier, an open second end in the chamber, and a sidewall extending therebetween, the open second end of the inlet being positioned to at least partially inhibit fluid and/or debris from collecting in an interior portion of the inlet;
   (c) a tangential outlet in the at least one sidewall of the housing through which the air flows substantially tangentially out of the chamber, wherein the tangential outlet is spaced apart from the inlet such that the fluid and/or debris is at least partially inhibited from collecting in the interior portion of the inlet; and
   (d) a drain outlet in the base of the housing for removing the fluid and/or debris from the ventilator system by evacuation through the chamber.

2. The humidifier adaptor of claim 1, wherein the housing comprises a cylindrical housing.

3. The humidifier adaptor of claim 1, wherein the inlet extends into the chamber such that at least a portion of the fluid and/or debris, which enters the chamber through the tangential outlet, collects in the chamber without collecting in the interior portion of the inlet.

4. The humidifier adaptor of claim 1, wherein the open second end of the inlet is spaced apart from the base of the housing by a vertical distance of about 2.5 cm to about 10 cm.

5. The humidifier adaptor of claim 1, wherein the first end of the inlet is external to the housing.

6. The humidifier adaptor of claim 1, wherein the sidewall of the inlet is integral with the base of the housing.

7. The humidifier adaptor of claim 1, wherein the inlet is configured to be mounted to an outflow port of the humidifier.

8. The humidifier adaptor of claim 1, wherein the tangential outlet is in an upper portion of the sidewall of the housing.

9. The humidifier adaptor of claim 1, wherein at least a portion of the tangential outlet is below the open second end of the inlet.

10. The humidifier adaptor of claim 1, wherein the tangential outlet comprises an external end outside of the housing configured to connect to an inhalation tube of the ventilator system and a sidewall extending from the external end to the housing.

11. The humidifier adaptor of claim 10, wherein the sidewall of the tangential outlet is integral with the sidewall of the housing.

12. The humidifier adaptor of claim 1, wherein a central axis of the inlet is generally perpendicular to a central axis of the tangential outlet.

13. The humidifier adaptor of claim 1, wherein a central axis of the tangential outlet is tangent to any co-planar arc centered on a central axis of the inlet.

14. The humidifier adaptor of claim 1, wherein an angle θ between a central axis of the tangential outlet and a line tangent to an arc defined by an inner surface of the sidewall of the housing at a point of intersection between the central axis of the tangential outlet and the arc is from 20° to 70°.

15. The humidifier adaptor of claim 1, wherein a central axis of the inlet is spaced apart from a central axis of the tangential outlet by a distance of about 10 mm to about 50 mm.

16. The humidifier adaptor of claim 1, wherein the drain outlet is configured to receive negative pressure from a suction source.

17. The humidifier adaptor of claim 16, wherein the drain outlet comprises a drain tube comprising a first end in the base of the housing and a second end, opposite the first end, configured to be connected to the suction source.

18. The humidifier adaptor of claim 17, wherein the drain tube is integral with the base of the housing.

19. The humidifier adaptor of claim 1, wherein the drain outlet comprises a valve for restricting fluid flow from the chamber through the drain outlet.

20. The humidifier adaptor of claim 1, further comprising a splash shield extending into the chamber from the top of the housing towards the open second end of the inlet, the splash shield being positioned to at least partially inhibit the fluid and/or debris from collecting in the interior portion of the inlet.

21. The humidifier adaptor of claim 20, wherein the sidewall of the inlet is cylindrical and the splash shield comprises an arcuate body sized to partially surround an outer surface of the sidewall of the inlet.

22. The humidifier adaptor of claim 1, wherein the housing comprises a port configured to receive a temperature probe for measuring a temperature in the chamber.

23. The humidifier adaptor of claim 1, further comprising a temperature probe, wherein the housing comprises a port configured to receive the temperature probe, such that a sensory portion of the probe is positioned in the chamber.

24. The humidifier adaptor of claim 1, wherein the adaptor is configured such that the air from the humidifier passes from the interior portion of the inlet to the chamber of the housing through the open second end of the inlet.

25. The humidifier adaptor of claim 1, comprising empty space extending from the open second end of the inlet to an underside of the top of the housing for permitting the air from the humidifier to pass directly from the interior portion of the inlet to the chamber of the housing.

26. The humidifier adaptor of claim 1, wherein the open second end of the inlet is uncovered.

27. A method for removing fluid and/or debris from a ventilator system, wherein the ventilator system comprises an inspiratory tube and an adaptor, the adaptor comprising:
  (a) a housing comprising a base, a top, and at least one sidewall extending therebetween, which together define a chamber;
  (b) an inlet in the base of the housing extending into the chamber, the inlet comprising a first end configured to receive air from a humidifier, an open second end in the chamber, and a sidewall extending therebetween, the open second end of the inlet being positioned to at least partially inhibit the fluid and/or debris from collecting in an interior portion of the inlet;
  (c) a tangential outlet in the at least one sidewall of the housing through which the air flows substantially tangentially out of the chamber to the inspiratory tube, wherein the tangential outlet is spaced apart from the inlet such that the fluid and/or debris is at least partially inhibited from collecting in the interior portion of the inlet;
  (d) and a drain outlet in the base of the housing for removing the fluid and/or debris from the ventilator system by evacuation through the chamber, the method comprising:
  tilting the inspiratory tube, thereby causing the fluid and/or debris in the inspiratory tube to pass through the inspiratory tube and outlet into the chamber defined by the housing; and
  actuating a suction source connected to the drain outlet to apply negative pressure to the chamber to evacuate the fluid and/or debris from the chamber through the drain outlet.

28. The method of claim 27, wherein the inlet is mounted to an outflow port of the humidifier.

29. The method of claim 27, wherein the drain outlet comprises a drain tube comprising a first end in the base of the housing and a second end, opposite the first end, configured to be connected to the suction source.

30. The method of claim 27, wherein the drain outlet further comprises a valve for restricting a flow of the fluid and/or debris from the chamber.

31. The method of claim 30, further comprising opening the valve so that the negative pressure from the suction source is applied to the chamber through the drain outlet.

32. The method of claim 30, further comprising closing the valve after the fluid and/or debris is removed from the chamber.

33. The method of claim 30, wherein the valve comprises a manually actuated valve which is opened or closed by pressing on a piston of the valve.

34. A method of assembling a ventilator system, comprising:
  connecting an inlet of a humidifier adaptor to a humidifier, wherein the humidifier adaptor comprises:
    (a) a housing comprising a base, a top, and at least one sidewall extending therebetween, which together define a chamber;
    (b) an inlet in the base of the housing extending into the chamber, the inlet comprising a first end configured to receive air from the humidifier, an open second end in the chamber, and a sidewall extending therebetween, the open second end of the inlet being positioned to at least partially inhibit fluid and/or debris from collecting in an interior portion of the inlet;
    (c) a tangential outlet in the at least one sidewall of the housing through which the air flows substantially tangentially out of the chamber, wherein the tangential outlet is spaced apart from the inlet such that the fluid and/or debris is at least partially inhibited from collecting in the interior portion of the inlet; and
    (d) a drain outlet in the base of the housing for removing the fluid and/or debris from the ventilator system by evacuation through the chamber;
  directly or indirectly connecting an end of an inspiratory tube to the outlet of the humidifier adaptor;
  connecting an opposite end of the inspiratory tube to a patient y-connector;
  connecting an expiratory tube to the patient y-connector; and
  connecting a ventilator to the ventilator system, such that the ventilator provides oxygenated airflow to the inspiratory tube through the humidifier and the humidifier adaptor.

35. The method of claim 34, further comprising connecting a patient side port of the y-connector to a patient interface assembly to conduct air to and from a patient.

36. The method of claim 34, wherein connecting the humidifier adaptor to the humidifier comprises inserting an outflow port of the humidifier into the inlet of the humidifier adaptor through the first end of the inlet.

37. The method of claim 34, wherein the drain outlet comprises a drain tube comprising an open first end in the base of the housing and an open second end, opposite the first end, the method further comprising connecting the open second end of the drain tube to a suction source for applying negative pressure to the chamber.

* * * * *